US007060107B2

(12) United States Patent
Bebot et al.

(10) Patent No.: US 7,060,107 B2
(45) Date of Patent: Jun. 13, 2006

(54) COMPOSITIONS FOR OXIDATION DYEING KERATIN FIBERS COMPRISING AT LEAST TWO PARTICULAR QUATERNARY POLYAMMONIUMS AND USES THEREOF

(75) Inventors: Cécile Bebot, Clichy (FR); Christine Rondeau, Sartrouville (FR); François Cottard, Levallois-Perret (FR); Francoise Boudy, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/750,717

(22) Filed: Jan. 2, 2001

(65) Prior Publication Data

US 2002/0013972 A1  Feb. 7, 2002

(30) Foreign Application Priority Data

Dec. 30, 1999  (FR) .................................. 99 16764

(51) Int. Cl.
*A61K 7/13* (2006.01)
(52) U.S. Cl. ...................... 8/405; 8/406; 8/407; 8/408; 8/409; 8/410; 8/412; 8/421; 8/552; 8/554; 8/568; 8/602; 8/606
(58) Field of Classification Search .............. 8/404, 8/405, 406, 407, 435, 408, 409, 410, 412, 8/421, 552, 554, 568, 602, 606; 424/78.02, 424/70.1, 70.13, 70.11, 70.17
See application file for complete search history.

(56) References Cited

U.S. PATENT DOCUMENTS

| | | | |
|---|---|---|---|
| 2,528,378 A | 10/1950 | Mannheimer | 260/309.6 |
| 2,781,354 A | 2/1957 | Mannheimer | 260/309.6 |
| 3,849,548 A * | 11/1974 | Grand | 424/70 |
| 3,915,921 A | 10/1975 | Schlatzer, Jr. | 260/17.4 |
| 3,986,825 A | 10/1976 | Sokol | 8/10.1 |
| 4,003,699 A | 1/1977 | Rose et al. | 8/10.2 |
| 4,157,388 A | 6/1979 | Christiansen | 424/70 |
| 4,314,807 A * | 2/1982 | Grollier et al. | 8/406 |
| 4,390,689 A | 6/1983 | Jacquet et al. | 528/335 |
| 4,509,949 A | 4/1985 | Huang et al. | 586/558 |
| 4,555,246 A | 11/1985 | Grollier et al. | 8/405 |
| 4,702,906 A | 10/1987 | Jacquet et al. | 424/70 |
| 4,719,282 A | 1/1988 | Nadolsky et al. | 528/310 |
| 4,820,308 A | 4/1989 | Madrange et al. | 8/405 |
| 4,842,849 A * | 6/1989 | Grollier et al. | 424/70.13 |
| 4,943,430 A | 7/1990 | Hefford et al. | 424/70 |
| 5,009,880 A * | 4/1991 | Grollier et al. | 424/47 |
| 5,061,289 A | 10/1991 | Clausen et al. | 8/405 |
| 5,380,340 A | 1/1995 | Neunhoeffer et al. | 8/409 |
| 5,538,517 A * | 7/1996 | Samain et al. | 8/423 |
| 5,735,908 A | 4/1998 | Cotteret et al. | 8/410 |
| 5,766,576 A | 6/1998 | Löwe et al. | 424/62 |
| 5,976,195 A * | 11/1999 | de la Mettrie et al. | 8/411 |
| 6,099,592 A | 8/2000 | Vidal et al. | 8/409 |
| 6,251,145 B1 * | 6/2001 | De La Mettrie et al. | 8/407 |

FOREIGN PATENT DOCUMENTS

| | | |
|---|---|---|
| DE | DT 23 59 399 | 11/1973 |
| DE | DD 213 835 | 3/1983 |
| DE | 38 43 892 | 12/1988 |
| DE | 41 33 957 | 10/1991 |
| DE | 195 43 988 | 11/1995 |
| EP | 0 557 203 | 8/1983 |
| EP | 0 173 109 | 8/1985 |
| EP | 0 216 479 | 8/1986 |
| EP | 0 673 641 | 9/1995 |
| EP | 0 960 617 | 12/1999 |
| FR | 2 080 759 | 11/1971 |
| FR | 2 190 406 | 2/1974 |
| FR | 2 733 749 | 11/1996 |
| FR | 2 750 048 | 12/1997 |
| FR | 2 773 992 | 7/1999 |
| GB | 1 026 978 | 4/1966 |
| GB | 1 153 196 | 5/1969 |
| GB | 2 188 948 | 10/1987 |
| JP | 9-110659 | 4/1997 |
| WO | WO 94/08969 | 4/1994 |
| WO | WO 94/08970 | 4/1994 |
| WO | WO 96/15765 | 5/1996 |
| WO | WO 99/17727 * | 4/1999 |

OTHER PUBLICATIONS

Co-pending U.S. Appl. No. 09/750,718; Title: Compositions for Oxidation Dyeing Keratin Fibers Comprising at Least One Thickening Polymer Comprising at Least One Oxidation Dye, at Least One Thickening Polymer Comprising at Least One Fatty Chain, and at Least One Fatty Alcohol Comprising More Than Twenty Inventors: François Cottard et al. filed Jan. 2, 2001.

Co-pending U.S. Appl. No. 09/750,757; Title: Compositions for Oxidation Dyeing Keratin Fibers Comprising at Least One Fatty Alcohol Having More Than Twenty Carbon Atoms and at Least One Oxyalkylenated Nonionic Surfactant With an HLB Greater Than 5 Inventors: François Cottard et al. filed Jan. 2, 2001.

Co-pending U.S. Appl. No. 09/750,716; Title: Compositions for Oxidation Dyeing Keratin Fibers Comprising at Least One Thickening Polymer Comprising at Least One Fatty Chain and at Least One Fatty Alcohol Chosen From Monoglycerolated Fatty Alcohols and Polyglycerolated Fatty Alcohols Inventors: François Cottard et al. filed Jan. 2, 2001.

(Continued)

*Primary Examiner*—Eisa Elhilo
(74) *Attorney, Agent, or Firm*—Finnegan, Henderson, Farabow, Garrett & Dunner, LLP

(57) ABSTRACT

Compositions for oxidation dyeing keratin fibers, such as human keratin fibers like hair, comprising, in a dyeing medium, (1) at least one oxidation dye, and (2) a combination comprising at least one cyclohomopolymer of dialkyl-diallylammonium and at least one other particular quaternary polyammonium. Processes comprising such oxidation dyeing compositions.

91 Claims, No Drawings

OTHER PUBLICATIONS

Porter et al. Handbook of Surfactants, 1991. pp. 117-178.
Fonnum et al., "Associative thickeners Part 1: Synthesis, rheology and aggregation behavior", Colloid & Polymer Science, vol. 271, No. 4, Apr. 1993, pp. 380-189.
English language Derwent Abstract of EP 0 557 203, Feb. 19, 1993.
English language Derwent Abstract of EP 0 960 617. Dec. 1, 1999.
English language Derwent Abstract of FR 2.080.759, Sep. 20, 1971.
English language Derwent Abstract of FR 2 750 048, Dec. 26, 1997.
English language Derwent Abstract of FR 2 773 992, Jul. 30, 1999.
English language Derwent Abstract of DD 213 835, Mar. 3, 1983.

* cited by examiner

COMPOSITIONS FOR OXIDATION DYEING KERATIN FIBERS COMPRISING AT LEAST TWO PARTICULAR QUATERNARY POLYAMMONIUMS AND USES THEREOF

The present invention relates to cosmetic compositions for oxidation dyeing keratin fibers, such as human keratin fibers like hair, comprising, in a dyeing medium, (1) at least one oxidation dye, and (2) a combination comprising at least one cyclohomopolymer of dialkyldiallylammonium and at least one other particular quaternary polyammonium.

It is known to dye keratin fibers, for example human hair, with dyeing compositions comprising oxidation dye precursors, generally called "oxidation bases." Representative oxidation bases include ortho- and para-phenylenediamines, ortho- and para-aminophenols, and heterocyclic bases.

Oxidation dye precursors are compounds initially only slightly colored or not colored that develop their dyeing power in the hair in the presence of oxidizing agents, leading to the formation of colored compounds. The formation of these colored compounds results either from oxidative condensation of the "oxidation bases" with themselves, or oxidative condensation of the "oxidation bases" with color-modifying compounds, or "couplers," which are generally present in the dyeing compositions used in oxidation dyeing. Representative couplers include meta-phenylenediamines, meta-aminophenols, meta-diphenols, and certain heterocyclic compounds.

The variety of compositions that can be employed in oxidation coloration, chosen from oxidation bases, oxidation couplers and mixtures of oxidation bases and couplers, can contribute to a pallet very rich in color.

The oxidizing agents which allow oxidative condensation generally may have an adverse effect on at least one property of the hair treated. The hair may become rough, difficult to disentangle and/or more fragile. To remedy at least one of the above-mentioned drawbacks, the use of certain quaternary polyammoniums has already been proposed in French patent 2,270,846, the disclosure of which is incorporated by reference herein.

However, the inventors have observed that the polymers mentioned above tended not to make it possible to sufficiently remedy at least one of the disadvantages while preserving or improving the dyeing properties.

The inventors have discovered that it is possible to obtain oxidation dyeing compositions with at least one improvement over previous dyeing compositions with respect to cosmetic properties. Additionally, such compositions may favor more intense and more chromatic (radiant) shades, while exhibiting low selectivities and good fastness toward chemical agents (shampoo, permanent waving and the like) and/or natural agents (light, perspiration and the like), and while offering the hair good cosmetic properties. The inventors have discovered that it is possible to obtain at least one of the aforementioned characteristics by formulating a cosmetic dyeing composition comprising (1) at least one oxidation dye, and (2) a combination comprising at least one cyclohomopolymer of dialkyldiallylammonium and at least one other particular quaternary polyammonium.

At least one of these discoveries forms the basis of the present invention.

The subject of the present invention is thus a cosmetic composition for oxidation dyeing keratin fibers, such as human keratin fibers like hair, comprising, in a dyeing medium (1) at least one oxidation dye, and (2) a combination comprising at least one cyclohomopolymer of dialkyldiallylammonium and at least one other particular quaternary polyammonium.

Another subject of the invention relates to a ready-to-use cosmetic composition for oxidation dyeing keratin fibers comprising, in a dyeing medium, (1) at least one oxidation dye, (2) a combination comprising at least one cyclohomopolymer of dialkyldiallylammonium and at least one other particular quaternary polyammonium, and (3) at least one oxidizing agent. The term "ready-to-use composition" is understood to mean, for the purposes of the present invention, a composition intended to be applied immediately to the keratin fibers, either stored as it is before use or obtained from the mixture of two or more compositions.

The invention also relates to a method for oxidation dyeing keratin fibers, such as human keratin fibers like hair, comprising:

(a) applying to said keratin fibers at least one dyeing composition (A) comprising, in a dyeing medium:
at least one oxidation dye, and
a combination comprising at least one cyclohomopolymer of dialkyldiallylammonium and at least one other particular quaternary polyammonium, (b) developing the color with the aid of at least one oxidizing composition (B) comprising at least one oxidizing agent, wherein said at least one oxidizing composition (B) is combined at the time of use with said at least one dyeing composition (A) or said at least one oxidizing composition (B) is applied sequentially to said at least one dyeing composition (A) without intermediate rinsing.

One variation of this method relates to a method for oxidation dyeing keratin fibers, such as human keratin fibers like hair, comprising:

(a) applying to said keratin fibers at least one dyeing composition (A) comprising, in a dyeing medium:
at least one oxidation dye, and
a combination comprising at least one cyclohomopolymer of dialkyldiallylammonium and at least one other particular quaternary polyammonium, and (b) developing the color with the aid of at least one oxidizing composition (B) comprising:
at least one oxidizing agent, and
a combination comprising at least one cyclohomopolymer of dialkyldiallylammonium and at least one other particular quaternary polyammonium, wherein said at least one oxidizing composition (B) is combined at the time of use with said at least one dyeing composition (A) or said at least one oxidizing composition (B) is applied sequentially to said at least one dyeing composition (A) without intermediate rinsing.

Another variation of the above-described method is a method for oxidation dyeing keratin fibers, such as human keratin fibers like hair, comprising:

applying to said keratin fibers at least one dyeing composition (A) comprising, in a dyeing medium, at least one oxidation dye, and developing the color with the aid of at least one oxidizing composition (B) comprising at least one oxidizing agent, wherein said oxidizing composition (B) comprises a combination comprising at least one cyclohomopolymer of dialkyldiallylammonium and at least one other particular quaternary polyammonium, or wherein said dyeing composition (A) and said oxidizing composition (B) separately comprise said at least one cyclohomopolymer of dialkyldiallylammonium or said at least one other particular quaternary polyammonium, and wherein said at least one oxidizing composition (B) is combined at the time of use with said at least one dyeing composition (A) or wherein said at least one oxidizing composition (B) is applied sequentially to said at least one dyeing composition (A) without intermediate rinsing.

For example, in one embodiment of the invention, said at least one cyclohomopolymer of dialkyldiallylammonium can be present in said at least one dyeing composition (A), and said at least one other particular quaternary polyammonium can be present in said at least one oxidizing composition (B). In another embodiment of the invention, said at least one cyclohomopolymer of dialkyldiallylammonium can be present in said at least one oxidizing composition (B), and said at least one other particular quaternary polyammonium can be present in said at least one dyeing composition (A).

One embodiment of the invention relates to multicompartment dyeing devices or "kits" for oxidation dyeing keratin fibers, such as human keratin fibers like hair.

A kit according to the invention comprises at least two compartments, wherein:

a first compartment comprises at least one oxidation dye and a combination comprising at least one cyclohomopolymer of dialkyldiallylammonium and at least one other particular quaternary polyammonium, and a second compartment comprises at least one oxidizing agent.

A variation of the above-mentioned kit according to the invention comprises at least two compartments, wherein:

a first compartment comprises at least one oxidation dye and a second compartment comprises at least one oxidizing agent and a combination comprising at least one cyclohomopolymer of dialkyldiallylammonium and at least one other particular quaternary polyammonium.

Another variation of the above-mentioned kit according to the invention comprises at least two compartments, wherein:

a first compartment comprises at least one oxidation dye and a combination comprising at least one cyclohomopolymer of dialkyldiallylammonium and at least one other particular quaternary polyammonium, and a second compartment comprises at least one oxidizing agent and a combination comprising at least one cyclohomopolymer of dialkyldiallylammonium and at least one other particular quaternary polyammonium.

A further variation of the above-mentioned kit according to the invention comprises at least two compartments, wherein:

a first compartment comprises at least one oxidation dye and at least one cyclohomopolymer of dialkyldiallylammonium and a second compartment comprises at least one oxidizing agent and at least one other particular quaternary polyammonium.

The above-mentioned kit can also comprise:

a first compartment comprising at least one oxidation dye and at least one particular quaternary polyammonium and a second compartment comprises at least one oxidizing agent and at least one cyclohomopolymer of dialkyldiallylammonium.

At least one cyclohomopolymer of dialkyldiallylammonium

The cyclohomopolymers of dialkyldiallylammonium according to the invention can be homopolymers comprising, as a constituent of the chain, at least one unit of structure (I):

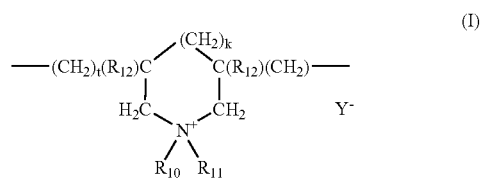

wherein:

k and t, which may be identical or different, are each chosen from 0 and 1, with the proviso that the sum of k+t is equal to 1;

$R_{12}$, which may be identical or different, are each chosen from hydrogen atoms and methyl groups;

$R_{10}$ and $R_{11}$, which may be identical or different, are each chosen from alkyl groups comprising from 1 to 22 carbon atoms, such as from 1 to 4 carbon atoms, hydroxyalkyl groups, such as hydroxy alkyl groups wherein the alkyl radical comprises from 1 to 5 carbon atoms, and $C_1$–$C_4$ amidoalkyl groups;

$R_{10}$ and $R_{11}$, together with the nitrogen atom to which they are commonly bonded, may additionally form at least one heterocyclic group, such as piperidyl groups and morpholinyl groups;

$Y^-$ is an anion, such as bromide, chloride, acetate, borate, citrate, tartrate, bisulfate, bisulfite, sulfate and phosphate. For example, such polymers are described in French patent 2,080,759 and in its Certificate of Addition 2,190,406, the disclosures of which are incorporated herein by reference.

One embodiment of the invention employs the polymer of formula (I) for which $R_{12}$ is hydrogen, $R_{10}$ and $R_{11}$ are methyl groups, and having a molecular mass, measured by Carbon-13 NMR of about 100,000.

Non-limiting examples of the polymers defined above include the dimethyldiallylammonium chloride homopolymer sold under the name "MERQUAT 100" by the company Calgon (and its homologues of low weight-average molecular mass).

The at least one other particular quaternary polyammonium polymer according to the invention can be chosen from:

(i) polymers comprising repeating units of formula (II):

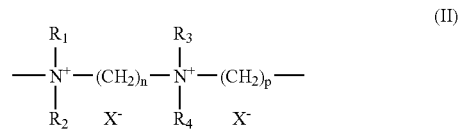

wherein:

$R_1$, $R_2$, $R_3$ and $R^4$, which may be identical or different, are each chosen from alkyl groups comprising from 1 to 4 carbon atoms and hydroxyalkyl groups comprising from 1 to 4 carbon atoms;

n and p, which may be identical or different, are each chosen from integers ranging from 2 to 20; and $X^-$ is an anion chosen from anions derived from inorganic acids and anions derived from organic acids.

Representative polymers of formula (II) include those in which $R_1$, $R_2$, $R_3$ and $R^4$ are chosen from methyl and ethyl groups and $X^-$ is a halogen atom such as a halogen chosen from chlorine, iodine and bromine.

Further, representative polymers of formula (II) include polymers in which $R_1$, $R_2$, $R_3$ and $R^4$ are methyl groups and n=3, p=6 and X=Cl, such as those of which the molecular weight, determined by gel-permeation chromatography, ranges from 9500 to 9900 and exemplified by formula (III):

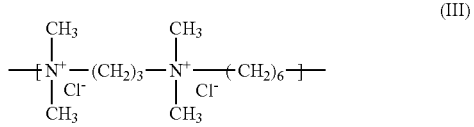

(III)

Other embodiments of the invention use polymers of formula (II) wherein $R_1$ and $R_2$ are methyl groups, $R_3$ and $R_4$ are ethyl groups and n=p=3 and X=Br, such as those of which the molecular weight, determined by gel-permeation chromatography, is approximately 1200 and exemplified by formula (IV):

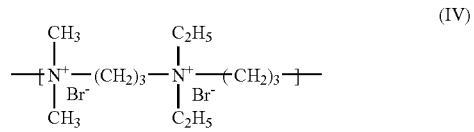

(IV)

Said quaternary polyammoniums of formula (II) are prepared as described in French Patent 2,270,846, the disclosure of which is incorporated by reference herein.

The at least one other particular quaternary polyammonium polymer according to the invention can also be chosen from:

(ii) polyquaternary ammonium polymers comprising repeating units of formula (V):

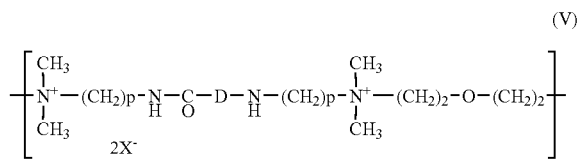

(V)

wherein:

p is an integer ranging from 1 to 6,

D is chosen from direct bonds and —$(CH_2)_r$—CO— groups, wherein r is a number equal to 4 or 7, and $X^-$ is an anion chosen from anions derived from inorganic acids and anions derived from organic acids.

Representative polyquaternary ammonium polymers comprising repeating units of formula (V) include those which have a molecular mass, measured by Carbon-13 NMR, of less than 100,000.

Among the polymers of formula (V) that may be mentioned include those for which:

a) D is a group —$(CH_2)_4$—CO—, $X^-$ is a chlorine atom, the molecular mass, measured by Carbon-13 NMR ($^{13}C$ NMR), is about 5600; for example, a polymer of this type is provided by the company Miranol under the name Mirapol-AD1, b) D is a group —$(CH_2)_7$—CO—, $X^-$ is a chlorine atom, the molecular mass, measured by Carbon-13 NMR ($^{13}C$ NMR), is about 8100; for example, a polymer of this type is provided by the company Miranol under the name Mirapol-AZ1, c) D is a direct bond, $X^-$ is a chlorine atom, the molecular mass, measured by Carbon-13 NMR ($^{13}C$ NMR), is about 25,500; for example, a polymer of this type is sold by the company Miranol under the name Mirapol-A15, d) formula (V) is a "Block Copolymer" comprising repeating units of each of the polymers described in paragraphs a) and c), which is for example provided by the company Miranol under the names Mirapol-9 ($^{13}C$ NMR molecular mass about 7800), Mirapol-175 ($^{13}C$ NMR molecular mass about 8000), Mirapol-95 ($^{13}C$ NMR molecular mass about 12500).

Another embodiment according to the invention is one in which in the polymer of formula (V) D is a direct bond, $X^-$ is a chlorine atom, the molecular mass, measured by Carbon-13 NMR ($^{13}C$ NMR), is about 25500.

Said quaternary polyammoniums of formula (V) may be prepared according to the methods described in U.S. Pat. Nos. 4,157,388, 4,390,689, 4,702,906, 4,719,282, the disclosures of which are incorporated by reference herein.

The at least one dialkyldiallylammonium cyclohomopolymer can be present in an amount ranging for example from 0.05% to 5% by weight relative to the total weight of the invention, such as for example from 0.1% to 3% by weight relative to the total weight of the invention.

The at least one quaternary polyammonium with units of formula (II) or (V) can be present in an amount ranging for example from 0.05% to 10% by weight relative to the total weight of the composition, such as for example from 0.2% to 5% by weight relative to the total weight of the composition.

In the composition, the weight ratio of the at least one quaternary polyammonium with units of formula (II) or (V) to the dialkyldiallylammonium cyclohomopolymer of formula (I) ranges for example from 0.1:1 to 50:1, such as from 1:1 to 10:1.

Oxidation Dyes

The at least one oxidation dye which can be used according to the present invention is chosen from oxidation bases, and oxidation couplers. In one embodiment, the compositions can comprise at least one oxidation base.

The oxidation bases usable in the context of the present invention are chosen from those conventionally known as oxidation dyes. Representative oxidation dyes include ortho- and para-phenylenediamines, double bases, ortho- and para-aminophenols and heterocyclic bases as well as their addition salts with an acid.

For example, the following oxidation bases may be used:

(I) para-phenylenediamines chosen from compounds of formula (VI), and their acid addition salts:

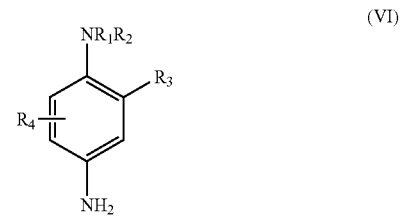

(VI)

wherein:

$R_1$ is chosen from hydrogen, $C_1$–$C_4$ alkyl groups, monohydroxy($C_1$–$C_4$ alkyl) groups, polyhydroxy($C_2$–$C_4$ alkyl) groups, ($C_1$–$C_4$)alkoxy ($C_1$–$C_4$)alkyl groups, phenyl groups, 4'-aminophenyl groups, and $C_1$–$C_4$ alkyl groups substituted with at least one group chosen from nitrogen-containing groups, $R_2$ is chosen from hydrogen, $C_1$–$C_4$ alkyl groups, monohydroxy($C_1$–$C_4$ alkyl) groups, polyhydroxy($C_2$–$C_4$ alkyl) groups, ($C_1$–$C_4$)alkoxy($C_1$–$C_4$)alkyl groups, and $C_1$–$C_4$ alkyl groups substituted with a nitrogen-containing group;

$R_1$ and $R_2$ may also form, together with the nitrogen atom to which they are bonded, a 5- or 6-membered nitrogen-containing heterocycle ring, optionally substituted with at least one group chosen from alkyl groups, hydroxyl groups and ureido groups;

$R_3$ is chosen from hydrogen, halogens, such as chlorine, $C_1$–$C_4$ alkyl groups, sulfo groups, carboxyl groups, monohydroxy($C_1$–$C_4$ alkyl) groups, hydroxy($C_1$–$C_4$ alkyoxy) groups, acetylamino($C_1$–$C_4$ alkoxy) groups, mesylamino ($C_1$–$C_4$ alkoxy) groups, and carbamoylamino($C_1$–$C_4$ alkoxy) groups;

$R_4$ is chosen from hydrogen, halogens, and $C_1$–$C_4$ alkyl groups.

Suitable nitrogen-containing groups of formula (VI) above may, for example, be chosen from amino, ($C_1$–$C_4$) monoalkylamino, ($C_1$–$C_4$)dialkylamino, ($C_1$–$C_4$)trialkylamino, monohydroxy($C_1$–$C_4$)alkylamino, imidazolinium, and ammonium groups.

Representative para-phenylenediamines of formula (VI) above which may be used include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine and their acid addition salts.

In other embodiments of the present invention, para-phenylenediamines of formula (VI) above can, for example, be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and their acid addition salts.

According to the invention, "double bases" is understood to mean the compounds comprising at least two aromatic rings on which at least one functional group chosen from amino groups and hydroxyl groups are carried.

(II) double bases chosen from compounds comprising at least two aromatic rings substituted with at least one group chosen from amino and hydroxyl groups. Such double bases may be chosen from compounds of formula (VII), and their acid addition salts:

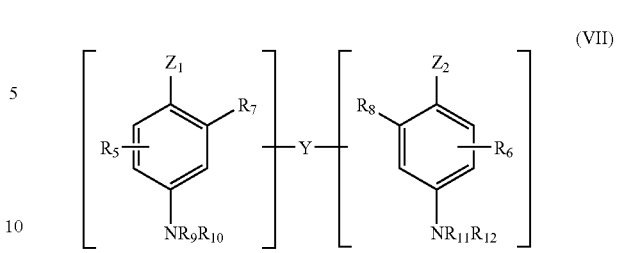

wherein:

$Z_1$ and $Z_2$, which may be identical or different, are each chosen from hydroxyl groups, and —$NH_2$ groups, optionally substituted with a group chosen from $C_1$–$C_4$ alkyl groups, and linkers Y;

linker Y is chosen from linear and branched, divalent alkylene groups comprising from 1 to 14 carbon atoms, optionally interrupted by, or optionally terminating with, at least one entity chosen from nitrogen-containing groups and heteroatoms such as oxygen, sulfur, and nitrogen, and optionally substituted with at least one group chosen from hydroxyl groups, and $C_1$–$C_6$ alkoxy groups;

$R_5$ and $R_6$, which may be identical or different, are each chosen from hydrogen, halogens, $C_1$–$C_4$ alkyl groups, monohydroxy($C_1$–$C_4$ alkyl) groups, polyhydroxy($C_2$–$C_4$ alkyl) groups, amino($C_1$–$C_4$ alkyl) groups, and linkers Y;

$R_7$, $R_8$, $R_9$, $R_{10}$, $R_{11}$ and $R_{12}$, which may be identical or different, are each chosen from hydrogen, linkers Y, and $C_1$–$C_4$ alkyl groups;

provided that said compounds of formula (VII) comprise only one linker Y per molecule.

Suitable nitrogen-containing groups of formula (VII) include mono($C_1$–$C_4$)alkylamino, ($C_1$–$C_4$)dialkylamino, ($C_1$–$C_4$)trialkylamino, monohydroxy($C_1$–$C_4$)alkylamino, imidazolinium and ammonium groups.

Representative double bases of formula (VII) include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and their acid addition salts.

In another embodiment of the invention, the double bases of formula (VII) may be chosen from N,N'-bis(β-hydroxyethyl)-N,N'-bis(4'-aminophenyl)-1,3 -diaminopropanol, 1,8-bis(2,5-diaminophenoxy)-3,5-dioxaoctane, and their acid addition salts.

(III) para-aminophenols chosen from compounds of formula (VIII), and their acid addition salts:

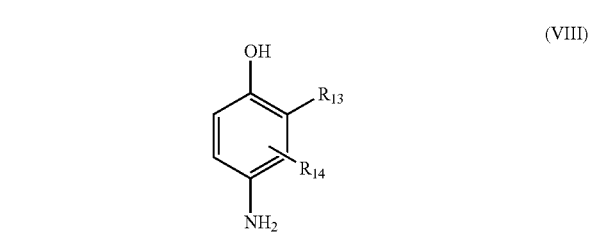

wherein:

$R_{13}$ is chosen from hydrogen, halogens, such as fluorine, $C_1$–$C_4$ alkyl groups, monohydroxy($C_1$–$C_4$ alkyl) groups, ($C_1$–$C_4$)alkoxy($C_1$–$C_4$)alkyl groups, amino($C_1$–$C_4$ alkyl), and hydroxy($C_1$–$C_4$)alkylamino($C_1$–$C_4$ alkyl) groups;

$R_{14}$ is chosen from hydrogen, halogens, such as fluorine, $C_1$–$C_4$ alkyl groups, monohydroxy($C_1$–$C_4$ alkyl) groups, polyhydroxy($C_2$–$C_4$ alkyl) groups, amino($C_1$–$C_4$ alkyl) groups, cyano($C_1$–$C_4$ alkyl) groups, and ($C_1$–$C_4$)alkoxy ($C_1$–$C_4$)alkyl groups.

Representative para-aminophenols of formula (VIII) above include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their acid addition salts.

(IV) ortho-aminophenols chosen, for example, from 2-aminophenol, 2-amino-1-hydroxy-5-methylbenzene, 2-amino-1-hydroxy-6-methylbenzene, 5-acetamido-2-aminophenol, and their acid addition salts.

(V) heterocyclic bases chosen, for example, from pyridine derivatives, pyrimidine derivatives, pyrazole derivatives, pyrazolo-pyrimidine derivatives, and their acid addition salts.

Representative pyridine derivatives include 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine, 3,4-diaminopyridine, and their acid addition salts. Some of the aforementioned pyridine derivatives have been described, for example in the patents GB 1,026,978 and GB 1,153,196, the disclosures of which are incorporated by reference herein.

Representative pyrimidine derivatives include 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their acid addition salts. Some of the aforementioned pyrimidine derivatives have been described, for example in German Patent DE 2,359,399, Japanese Patents JP 88-169,571 and JP 91-10659, and Patent Application WO 96/15765, the disclosures of which are incorporated by reference herein.

Representative pyrazolo-pyrimidine derivatives include those described, for example, in the patent application FR-A-2 750 048, the disclosure of which is incorporated by reference herein. Such pyrazolo-pyrimidine derivatives include pyrazolo[1,5-a]pyrimidines, such as
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
3-amino-5-methyl-7-imidazolylpropylaminopyrazolo[1,5-a]pyrimidine;
their salts, such as their acid addition salts, and their tautomeric forms when a tautomeric equilibrium exists.

Representative pyrazole derivatives include 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their acid addition salts. Some of the aforementioned pyrazole derivatives have been described, for example in Patents DE 3,843,892, DE 4,133, 957 and Patent Applications WO 94/08969, WO 94/08970, FR-A-2,733,749 and DE 195 43 988, the disclosures of which are incorporated by reference herein.

In accordance with the present invention, the oxidation bases are generally present in an amount ranging for example from 0.0005% to 12% by weight relative to the total weight of the composition, such as for example from 0.005% to 8% by weight relative to the total weight of the composition.

Suitable couplers which may be used in the dyeing process of the invention include couplers conventionally used in oxidation dyeing compositions. Such couplers can be chosen, for example, from meta-phenylenediamines, meta-aminophenols, meta-diphenols, naphthols, sesamol and its derivatives, heterocyclic couplers, such as, for example, indole derivatives, indoline derivatives, pyridine derivatives, pyrazolotriazole derivatives, pyrazolones, indazoles, benzimidazoles, benzothiazoles, benzoxazoles, 1,3-benzodioxoles, quinolines and their acid addition salts.

Representative couplers include 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 1-amino-2-methoxy-4,5-methylenedioxybenzene, 2-amino-3-hydroxypyridine, 3,6-dimethylpyrazolo[3,2-c]-1,2,4-triazole, 2,6-dimethylpyrazolo[1,5-b]-1,2,4-triazole, and their acid addition salts.

When these couplers are present, they are generally present in an amount ranging for example from 0.0001% to 10% by weight relative to the total weight of the composition, such as for example from 0.005% to 5% by weight relative to the total weight of the composition.

Generally, the acid addition salts of the oxidation bases and couplers can be chosen from hydrochlorides, hydrobromides, sulfates, tartrates, lactates and acetates.

The compositions according to the invention may also comprise at least one direct dye. Representative direct dyes which can be used in the present invention include direct dyes that have conventionally been used in direct dyeing compositions and lighting direct dyeing compositions. For example, the dyes can be chosen from neutral, cationic, and anionic nitro dyes, neutral, cationic, and anionic anthraquinone dyes, and neutral, cationic, and anionic azo dyes. Generally, the direct dyes are present in amounts ranging for example from 0.001% to 20% by weight of the total weight of the composition, such as for example from 0.01% to 10% by weight of the total weight of the composition.

In one embodiment of the invention, namely within the ready-to-use composition, said at least one dyeing composition (A) and said at least one oxidizing composition (B) can optionally further comprise at least one thickening polymer chosen from nonionic, anionic, and cationic polymers comprising at least one fatty chain.

At Least One Thickening Polymer Comprising at Least One Fatty Chain

The at least one thickening polymer comprising at least one fatty chain according to the invention can be chosen from nonionic, anionic and cationic thickening polymers comprising at least one fatty chain.

(i) Anionic Thickeners

Such anionic thickening polymers comprising at least one fatty chain can be chosen from:

(I) anionic polymers comprising at least one hydrophilic unit and at least one allyl ether unit comprising at least one fatty chain, for example said anionic polymers wherein said at least one hydrophilic unit comprises at least one ethylenic unsaturated anionic monomeric residue, such as vinylcarboxylic acid and further such as at least one monomeric residue chosen from acrylic acid and methacrylic acid residues, and wherein said at least one allyl ether unit comprising at least one fatty chain corresponds to the monomeric residue resulting from the monomer of formula (IX):

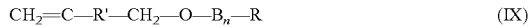

in which R' is chosen from H and $CH_3$, B is chosen from ethyleneoxy groups, n is chosen from zero and integers ranging from 1 to 100, R is a hydrocarbon group chosen from alkyl, arylalkyl, aryl, alkylaryl and cycloalkyl groups, comprising from 8 to 30 carbon atoms, such as from 10 to 24, and further such as from 12 to 18 carbon atoms. One embodiment of the invention comprises at least one allyl ether unit of the monomeric residue resulting from the monomer of formula (IX), wherein R' is H, n is equal to 10, and R is a stearyl ($C_{18}$) group.

Representative anionic amphiphilic polymers of this type are described and prepared, according to a method of emulsion polymerization, in patent EP-0,216,479, the disclosure of which is incorporated by reference herein.

As used herein, the term "lower alkyl" means an alkyl chosen from saturated and unsaturated, branched and unbranched $C_1$–$C_6$ alkyl groups.

Representative anionic thickening polymers comprising at least one fatty chain include for example polymers formed from 20% to 60% by weight of at least one monomer chosen from acrylic acid and methacrylic acid, 5% to 60% by weight of $C_1$–$C_6$ alkyl(meth)acrylates, 2% to 50% by weight of allyl ether comprising at least one fatty chain of formula (IX), and up to 1% by weight of a crosslinking agent chosen from well known copolymerizable polyethylenic unsaturated monomers such as diallyl phthalate, allyl (meth)acrylate, divinylbenzene, (poly)ethylene glycol dimethacrylate and methylenebisacrylamide.

One embodiment could comprise at least one anionic thickening polymer chosen from crosslinked terpolymers of methacrylic acid, ethyl acrylate, and polyethylene glycol (10 EO) stearyl alcohol ether (Steareth 10), such as the products sold by the company ALLIED COLLOIDS under the names SALCARE SC 80 and SALCARE SC 90, which are aqueous emulsions comprising 30% of a crosslinked terpolymer of methacrylic acid, of ethyl acrylate and of steareth-10-allyl ether (40/50/10).

Anionic thickening polymers comprising at least one fatty chain can also be chosen from:

(II) anionic polymers comprising at least one hydrophilic unit of the olefinic unsaturated carboxylic acid type and at least one hydrophobic unit of the ($C_{10}$–$C_{30}$)alkyl ester of unsaturated carboxylic acid type.

Such polymers are chosen from polymers comprising:
at least one hydrophilic unit formed from olefinic unsaturated carboxylic acid monomers of formula (X):

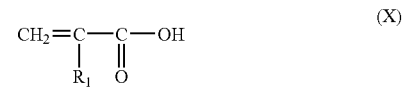

in which $R_1$ is chosen from H, $CH_3$, and $C_2H_5$, (which corresponds with acrylic acid, methacrylic acid and ethacrylic acid units), and at least one hydrophobic unit formed from ($C_{10}$–$C_{30}$)alkyl esters of unsaturated carboxylic acid monomers of formula (XI):

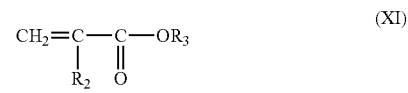

in which $R_2$ is chosen from H, $CH_3$, and $C_2H_5$, (which corresponds with acrylate, methacrylate and ethacrylate units) and $R_3$ is chosen from saturated and unsaturated, branched and unbranched $C_{10}$–$C_{30}$ alkyl groups. In one embodiment, for example, $R_2$ is chosen from H (acrylate units) and $CH_3$ (methacrylate units) and $R_3$ is chosen from $C_{12}$–$C_{22}$ alkyl groups.

($C_{10}$–$C_{30}$)alkyl esters of unsaturated carboxylic acids in accordance with the invention include for example lauryl acrylate, stearyl acrylate, decyl acrylate, isodecyl acrylate, dodecyl acrylate, lauryl methacrylate, stearyl methacrylate, decyl methacrylate, isodecyl methacrylate, and dodecyl methacrylate.

Anionic polymers of this type are for example described and prepared according to U.S. Pat. Nos. 3,915,921 and 4,509,949, the disclosures of which are incorporated by reference herein.

Anionic thickening polymers comprising at least one fatty chain that can be used include polymers formed from a mixture of monomers comprising:

(i) acrylic acid, (ii) at least one ester of formula (XI) described above wherein $R_2$ is chosen from H and $CH_3$, and $R_3$ is chosen from alkyl groups comprising from 12 to 22 carbon atoms, and (iii) at least one crosslinking agent chosen from well known copolymerizable polyethylenic unsaturated monomers such as diallyl phthalate, allyl (meth)acrylate, divinylbenzene, (poly)ethylene glycol dimethacrylate and methylenebisacrylamide.

Representative anionic thickening polymers comprising at least one fatty chain that can be used include (i) polymers comprising 95% to 60% by weight of acrylic acid monomeric residue (hydrophilic unit), 4% to 40% by weight of $C_{10}$–$C_{30}$ alkyl acrylate monomeric residue (hydrophobic unit), and 0% to 6% by weight of crosslinking polymerizable monomeric residue, and (ii) polymers comprising 98% to 96% by weight of acrylic acid monomeric residue (hydrophilic unit), 1% to 4% by weight of $C_{10}$–$C_{30}$ alkyl acrylate monomeric residue (hydrophobic unit) and 0.1% to 0.6% by weight of crosslinking polymerizable monomeric residue such as those described above.

Among the above polymers, the products sold by the company GOODRICH under the trade names PEMULEN TR1, PEMULEN TR2, and CARBOPOL 1382 can be used. One embodiment could employ at least one polymer chosen from PEMULEN TR1, and the product sold by the company S.E.P.P.I.C. under the name COATEX SX.

Anionic thickening polymers comprising at least one fatty chain can also be chosen from:

(III) terpolymers formed from maleic anhydride/$C_{30}$–$C_{38}$ α-olefin/alkyl maleate such as the product (maleic anhydride/$C_{30}$–$C_{38}$ α-olefin/isopropyl maleate copolymer) sold under the name PERFORMA V 1608 by the company NEWPHASE TECHNOLOGIES, (IV) acrylic terpolymers formed from:

(a) 20% to 70% by weight of a carboxylic acid with α,β-monoethylenic unsaturation (b) 20% to 80% by weight of a nonsurfactant monomer with α,β-monoethylenic unsaturation different from (a)

(c) 0.5% to 60% by weight of a nonionic monourethane which is the product of the reaction of a monohydric surfactant with a monoisocyanate with monoethylenic unsaturation such as acrylic terpolymers described in patent application EP-A-0,173,109, the disclosure of which is incorporated by reference herein, and more particularly acrylic terpolymers described therein in Example 3, namely a methacrylic acid/methyl acrylate/dimethyl metaisopropenyl benzyl isocyanate of ethoxylated (40 EO) behenyl alcohol terpolymer in 25% aqueous dispersion, (V) copolymers formed from at least two monomers, wherein at least one of said at least two monomers is chosen from a carboxylic acid with α,β-monoethylenic unsaturation, an ester of a carboxylic acid with α,β-monoethylenic unsaturation, and an oxyalkylenated fatty alcohol, and (VI) copolymers formed from at least three monomers, wherein at least one of said at least three monomers is chosen from a carboxylic acid with α,β-monoethylenic unsaturation, at least one of said at least three monomers is chosen from an ester of a carboxylic acid with α,β-monoethylenic unsaturation and at least one of said at least three monomers is chosen from an oxyalkylenated fatty alcohol.

Additionally, these compounds can also comprise, as monomer, a carboxylic acid ester comprising an α,β-monoethylenic unsaturation and a $C_1$–$C_4$ alcohol. By way of example of this type of compound, there may be mentioned ACULYN 22 sold by the company ROHM and HAAS, which is an oxyalkylenated stearyl methacrylate/ethyl acrylate/methacrylic acid terpolymer.

(ii) Nonionic Thickeners

Nonionic thickening polymers comprising at least one fatty chain according to the invention can be chosen from:

(1) celluloses modified by at least one group comprising at least one fatty chain such as:

hydroxyethylcelluloses modified by at least one group comprising at least one fatty chain such as alkyl, arylalkyl and alkylaryl groups and further such as alkyl, arylalkyl and alkylaryl groups wherein said alkyl groups comprise from 8–22 carbon atoms, such as the product NATROSOL PLUS GRADE 330 CS ($C_{16}$ alkyls) sold by the company AQUALON, and the product BERMOCOLL EHM 100 sold by the company BEROL NOBEL, hydroxyethylcelluloses modified by at least one polyalkylene glycol ether of alkylphenol group, such as the product AMERCELL POLYMER HM-1500 (polyethylene glycol (15) ether of nonylphenol) sold by the company AMERCHOL;

(2) hydroxypropylguars modified by at least one group comprising at least one fatty chain such as the product ESAFLOR HM 22 ($C_{22}$ alkyl chain) sold by the company LAMBERTI, the products RE 210-18 ($C_{14}$ alkyl chain) and RE 205-1 ($C_{20}$ alkyl chain) sold by the company RHONE POULENC (Succeeded by RHODIA CHIMIE);

(3) copolymers formed from vinylpyrrolidone and at least one hydrophobic monomer comprising at least one fatty chain such as for example:

the products ANTARON V216 and GANEX V216 (vinylpyrrolidone/hexadecene copolymer) sold by the company I.S.P., and the products ANTARON V220 and GANEX V220 (vinylpyrrolidone/eicosene copolymer) sold by the company I.S.P.;

(4) copolymers formed from at least one $C_1$–$C_6$ alkyl methacrylate and at least one amphiphilic monomer comprising at least one fatty chain and copolymers formed from at least one $C_1$–$C_6$ alkyl acrylate and at least one amphiphilic monomer comprising at least one fatty chain such as for example the oxyethylenated stearyl acrylate/methyl acrylate copolymer sold by the company GOLDSCHMIDT under the name ANTIL 208;

(5) copolymers formed from at least one hydrophilic methacrylate and at least one hydrophobic monomer comprising at least one fatty chain and copolymers formed from at least one hydrophilic acrylate and at least one hydrophobic monomer comprising at least one fatty chain such as for example the polyethylene glycol methacrylate/lauryl methacrylate copolymer;

(6) polyether-polyurethanes comprising in their chain both hydrophilic sequences which are most often of a polyoxyethylenated nature and hydrophobic sequences which may be chains chosen from aliphatic chains, cycloaliphatic chains, and aromatic chains;

(7) polymers comprising an aminoplast ether backbone possessing at least one fatty chain, such as the compounds PURE THIX provided by the company SUD-CHEMIE.

Nonionic thickening polymers can additionally include polyether-polyurethanes comprising at least two lipophilic (i.e., hydrophobic) hydrocarbon chains, comprising from 6 to 30 carbon atoms, separated by a hydrophilic sequence, it being possible for the hydrocarbon chains to be chosen from pendant chains and chains at the end of a hydrophilic sequence. One embodiment may comprise at least one pendant chain. In addition, the polymer may comprise a hydrocarbon chain at at least one end of a hydrophilic sequence.

Representative polyether-polyurethanes useful in the present invention may be polyblocks, such as in triblock form. The hydrophobic sequences may be at each end of the chain (for example: triblock copolymer with hydrophilic central sequence) and optionally both at the ends and in the chain (polyblock copolymer for example). These same polymers may also be in the form of graft units or may be star-shaped.

The nonionic polyether-polyurethanes comprising at least one fatty chain may be triblock copolymers whose hydrophilic sequence is a polyoxyethylenated chain comprising from 50 to 1000 oxyethylenated groups. Certain nonionic polyether-polyurethanes comprise a urethane bond between the hydrophilic sequences.

By extension, those whose hydrophilic sequences are linked by other chemical bonds to the lipophilic sequences are also included among the nonionic polyether-polyurethanes comprising at least one fatty chain.

Representative nonionic polyether-polyurethanes comprising at least one fatty chain include Rhéolate 205 comprising a urea function sold by the company RHEOX and Rhéolate 208, 204 and 212, as well as Acrysol RM 184, Aculyn 44 and Aculyn 46 from the company ROHM and HAAS [ACULYN 46 is a polycondensate of polyethylene glycol comprising 150 or 180 mol of ethylene oxide, stearyl alcohol and methylenebis(4-cyclohexylisocyanate) (SMDI), at 15% by weight in a maltodextrin (4%) and water (81%) matrix; ACULYN 44 is a polycondensate of polyethylene glycol comprising 150 or 180 mol of ethylene oxide, decyl alcohol and methylenebis(4-cyclohexylisocyanate) (SMDI), at 35% by weight in a propylene glycol (39%) and water (26%) mixture].

There may also be mentioned the product ELFACOS T210 comprising a $C_{12}$–$C_{14}$ alkyl chain and the product ELFACOS T212 comprising a $C_{18}$ alkyl chain from AKZO.

The product DW 1206B from RHOM & HAAS comprising a $C_{20}$ alkyl chain and with a urethane bond, sold at 20% dry matter content in water, may also be used.

It is also possible to use solutions and dispersions of these polymers for example in water and for example in an aqueous-alcoholic medium. By way of example of such polymers, there may be mentioned Rhéolate 255, Rhéolate 278 and Rhéolate 244 sold by the company RHEOX. It is also possible to use the product DW 1206F and DW 1206J provided by the company ROHM & HAAS.

Representative polyether-polyurethanes that can be used according to the invention include polyether-polyurethanes described in the article by G. Fonnum, J. Bakke and Fk. Hansen—Colloid Polym. Sci 271, 380, 389 (1993), the disclosure of which is incorporated by reference herein.

(iii) Cationic Thickeners

As used herein, "cationic thickener" refers to polymers chosen from polymers comprising at least one cationic group and polymers comprising at least one group which can be ionized to form cationic groups.

Representative cationic thickening polymers comprising at least one fatty chain used in the present invention can be chosen from quaternized cellulose derivatives and polyacrylates with noncyclic amine-containing side groups.

Such quaternized cellulose derivatives can be chosen from:

quaternized celluloses modified by groups comprising at least one fatty chain, such as at least one group chosen from alkyl, arylalkyl and alkylaryl groups comprising at least 8 carbon atoms, quaternized hydroxyethylcelluloses modified by at least one group comprising at least one fatty chain, such as at least one group chosen from alkyl, arylalkyl and alkylaryl groups comprising at least 8 carbon atoms.

In one embodiment, said alkyl groups carried by the above quaternized celluloses and hydroxyethylcelluloses comprise from 8 to 30 carbon atoms and the aryl groups are chosen from phenyl, benzyl, naphthyl and anthryl groups.

There may be mentioned as examples of quaternized alkylhydroxyethylcelluloses comprising at least one $C_8$–$C_{30}$ fatty chain the products QUATRISOFT LM 200, QUATRISOFT LM-X 529-18-A, QUATRISOFT LM-X 529-18B ($C_{12}$ alkyl) and QUATRISOFT LM-X 529-8 ($C_{18}$ alkyl) marketed by the company AMERCHOL and the products CRODACEL QM, CRODACEL QL ($C_{12}$ alkyl) and CRODACEL QS ($C_{18}$ alkyl) marketed by the company CRODA.

Representative polyacrylates with amine-containing side groups, quaternized and otherwise, comprise for example hydrophobic groups of the steareth 20 type (polyoxyethylenated stearyl alcohol (20)).

As examples of polyacrylates with amine-containing side groups, there may be mentioned the polymers 8781-121 B or 9492-103 from the company NATIONAL STARCH.

One embodiment of the oxidation dyeing composition according to the invention may comprise at least one nonionic thickening polymer comprising at least one fatty chain.

The at least one thickening polymer comprising at least one fatty chain is generally present in an amount ranging for example from 0.01% to 10% by weight relative to the total weight of the dyeing composition, such as from 0.1% to 5% by weight relative to the total weight of the dyeing composition.

Surfactants

The ready-to-use composition according to the invention can comprise at least one surfactant, which is present in at least one of said at least one dyeing composition (A), said at least one oxidizing composition (B), and said at least one dyeing composition (A) and said at least one oxidizing composition (B).

The at least one surfactant may be chosen from anionic, amphoteric, nonionic, zwitterionic and cationic surfactants.

Representative choices for the at least one surfactant include the following:

(i) Anionic Surfactant(s):

Representative anionic surfactants include salts (for example alkaline salts, such as sodium salts, ammonium salts, amine salts, amino alcohol salts and magnesium salts) of the following compounds: alkyl sulfates, alkyl ether sulfates, alkylamidoether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl($C_6$–$C_{24}$) sulfosuccinates, alkyl($C_6$–$C_{24}$) ether sulfosuccinates, alkyl($C_6$–$C_{24}$) amide sulfosuccinates, alkylsulfosuccinamates alkyl ($C_6$–$C_{24}$) sulfoacetates, acyl($C_6$–$C_{24}$) sarcosinates, acyl ($C_6$–$C_{24}$) glutamates, acyl isethionates, N-acyltaurates, and alkyl($C_6$–$C_{24}$)polyglycoside carboxylic esters such as alkylglucoside citrates, alkylpolyglycoside tartrate, alkylpolyglycoside sulfosuccinates, and alkyl sulfosuccinamates. The alkyl and acyl radicals of all of these various compounds can for example comprise from 12 to 20 carbon atoms, and the aryl radicals can for example be chosen from phenyl and benzyl groups.

For example, anionic surfactants can be chosen from fatty acid salts such as the salts of oleic acid, ricinoleic acid, palmitic acid, stearic acid, the acids of copra oil and the acids of hydrogenated copra oil, and acyl lactylates in which the acyl radical comprises from 8 to 20 carbon atoms. At least one weakly anionic surfactant can also be used, such as alkyl-D-galactosideuronic acids and their salts, as well as polyoxyalkylenated carboxylic ($C_6$–$C_{24}$)alkyl ether acids, polyoxyalkylenated carboxylic ($C_6$–$C_{24}$)alkylaryl ether acids, polyoxyalkylenated carboxylic ($C_6$–$C_{24}$)alkyl amidoether acids and their salts, for example, those comprising from 2 to 50 ethylene oxide groups.

(ii) Nonionic Surfactant(s):

Useful nonionic surfactants include compounds that are well known per se (see for example in this respect "Handbook of Surfactants" by M. R. Porter, published by Blackie & Son (Glasgow and London), 1991, pp. 116–178), the disclosure of which is incorporated by reference herein. Thus, nonionic surfactants can include alcohols, α-diols, and polyethoxylated alkylphenols and polypropoxylated alkylphenols comprising at least one fatty chain comprising for example from 8 to 18 carbon atoms, wherein the number of ethylene oxide and propylene oxide groups can range for example from 2 to 50. Additionally, copolymers of ethylene oxide, copolymers of propylene oxide, condensates of ethylene oxide with fatty alcohols, condensates of propylene oxide with fatty alcohols, polyethoxylated fatty amides, such as those comprising from 2 to 30 mol of ethylene oxide, polyglycerolated fatty amides on average comprising 1 to 5 glycerol groups, such as from 1.5 to 4, polyethoxylated fatty amines comprising for example from 2 to 30 mol of ethylene oxide, oxyethylenated fatty acid esters of sorbitan comprising from 2 to 30 mol of ethylene oxide, fatty acid esters of sucrose, fatty acid esters of polyethylene glycol, alkylpolyglycosides, N-alkylglucamine derivatives, amine oxides, such as the oxides of $(C_{10}-C_{14})$ alkylamines, and N-acylaminopropylmorpholine oxides can also be used. It will be noted that the alkylpolyglycosides are nonionic surfactants that can be suitable in the context of the present invention.

(iii) Amphoteric or Zwitterionic Surfactant(s):

Representative amphoteric and zwitterionic surfactants can be chosen from aliphatic secondary and tertiary amine derivatives in which the aliphatic radical is chosen from linear and branched chain radicals comprising 8 to 18 carbon atoms and comprising at least one water-soluble anionic group (chosen for example from carboxylate, sulfonate, sulfate, phosphate and phosphonate); mention may also be made of $(C_8-C_{20})$alkylbetaines, sulfobetaines, $(C_8-C_{20})$ alkylamido$(C_1-C_6)$alkylbetaines and $(C_8-C_{20})$alkylamido $(C_1-C_6)$alkylsulfobetaines. Representative amine derivatives include the products sold under the name MIRANOL, as described in U.S. Pat. Nos. 2,528,378 and 2,781,354, the disclosures of which are incorporated by reference herein, and classified in the CTFA dictionary, $3^{rd}$ edition, 1982, under the names Amphocarboxyglycinates and Amphocarboxypropionates, having the respective structures:

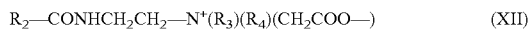

$$R_2-CONHCH_2CH_2-N^+(R_3)(R_4)(CH_2COO-) \quad (XII)$$

in which:

$R_2$ is chosen from alkyl groups derived from an acid $R_2$—COOH present in hydrolysed copra oil, and heptyl, nonyl and undecyl radicals, $R_3$ is a beta-hydroxyethyl group, and —$R_4$ is a carboxymethyl group;

and

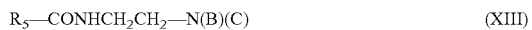

$$R_5-CONHCH_2CH_2-N(B)(C) \quad (XIII)$$

in which:

(B) is —$CH_2CH_2OX'$, wherein X' is an entity chosen from a —$CH_2CH_2$—COOH group and a hydrogen atom, (C) is —$(CH_2)_z$—Y', wherein z=1 or 2, and wherein Y' is an entity chosen from —COOH and —$CH_2$—CHOH—$SO_3H$ groups, $R_5$ is chosen from alkyl groups, such as (a) alkyl groups of an acid $R_5$—COOH present in oils chosen from copra oil and hydrolysed linseed oil, (b) alkyl groups, such as $C_7$, $C_9$, $C_{11}$ and $C_{13}$ alkyl groups, and (c) $C_{17}$ alkyl groups and the iso forms, and unsaturated $C_{17}$ groups.

Such representative compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of example, mention may be made of the cocoamphodiacetate sold under the trade name MIRANOL C2M Concentrate by the company RHODIA CHIMIE.

(iv) Cationic Surfactants:

Representative cationic surfactants include salts of optionally polyoxyalkylenated primary, secondary and tertiary fatty amines; quaternary ammonium salts such as tetraalkylammonium, alkylamidoalkyltrialkylammonium, trialkylbenzylammonium, and trialkylhydroxyalkylammonium, alkylpyridinium chlorides, alkylpyridinium bromides, imidazoline derivatives; and amine oxides of cationic nature.

In one embodiment, in the ready-to-use composition according to the invention, the dyeing composition (A) comprises at least one nonionic surfactant.

The at least one surfactant may be present in the composition according to the invention generally in an amount ranging for example from 0.01% to 40% by weight relative to the total weight of the composition, such as from 0.1% to 30% by weight relative to the total weight of the composition.

The ready-to-use composition according to the present invention may eventually comprise, in said at least one dyeing composition (A), in said at least one oxidizing composition (B), or both said at least one dyeing composition (A) and said at least one oxidizing composition (B), at least one other agent for adjustment of rheology, such as agents chosen from cellulose thickeners (for example, hydroxyethylcellulose, hydroxypropylcellulose, and carboxymethylcellulose), guar gum and its derivatives (for example, hydroxypropylguar), gums of microbial origin (for example, xanthan gum and scieroglucan gum), and synthetic thickeners (for example, crosslinked homopolymers of acrylic acid and crosslinked homopolymers of acrylamidopropanesulfonic acid.

Generally, these thickeners may be present in an amount ranging for example from 0.01% to 10% by weight relative to the total weight of the composition.

The medium of the composition appropriate for dyeing can be an aqueous medium, optionally comprising at least one cosmetically acceptable organic solvent.

Representative organic solvents may be chosen from alcohols, such as ethyl alcohol, isopropyl alcohol, benzyl alcohol, and phenylethyl alcohol. The organic solvents may also be chosen from glycols (for example, ethyleneglycol, propyleneglycol, butyleneglycol, dipropyleneglycol, and diethyleneglycol) and ethers of glycols (for example, monomethyl, monoethyl and monobutyl ethers of ethyleneglycol and for example monomethyl ether of propyleneglycol and alkyl ethers of diethyleneglycol glycol, such as, for example, monoethylether and monobutylether of diethyleneglycol).

The organic solvents are generally present in an amount ranging for example from 0.5% to 20% by weight relative to the total weight of the composition, such as from 2% to 10% by weight relative to the total weight of the composition.

The composition according to the invention may further comprise an effective quantity of other agents. For example, agents that are already known for oxidation coloration, such as various ordinary adjuvants including sequesterizers such as EDTA and etidronic acid, UV-screening agents, waxes, volatile and nonvolatile, cyclic and non-cyclic, linear and branched, organomodified (such as by amine groups) silicones, preservatives, ceramides, pseudoceramides, vegetable, mineral and synthetic oils, vitamins and provitamins such as panthenol, and opacifiers, may be included.

The composition can also comprise at least one agent chosen from reducing agents and antioxidants. Representative additional agents may include sodium sulfite, thioglycolic acid, thiolactic acid, sodium bisulfite, dehydroascorbic acid, hydroquinone, 2-methylhydroquinone, tert-butylhydroquinone and homogentisic acid. Generally, such agents may be present in the an amount ranging for example from 0.05% to 3.0% by weight relative to the total weight of the composition, such as from 0.05% to 1.5% by weight relative to the total weight of the composition.

The composition according to the invention may also comprise at least one fatty alcohol. The expression fatty alcohols includes, but is not limited to, linear and branched, saturated and unsaturated fatty alcohols. The expression at least one (as used herein, "at least one" means one or more and thus includes mixtures and combinations) fatty alcohol includes, but is not limited to, lauryl, cetyl, stearyl and oleyl alcohols. These additional fatty alcohols may be present in an amount ranging for example from 0.001% to 20% by weight relative to the total weight of the composition.

One skilled in the art should take care to select said optionally complementary compounds, such that the advantageous properties intrinsically associated with the dye composition according to the invention are not, or are not substantially, adversely affected by the additions envisaged.

In the ready-to-use composition, said at least one oxidizing composition (B) may comprise at least one oxidizing agent chosen, for example, from hydrogen peroxide, urea peroxide, alkali metal bromates and ferricyanides, and persalts such as perborates and persulfates. More specifically, hydrogen peroxide may be used. This oxidizing agent can be an oxygenated aqueous solution of which the titre may range from 1 to 40 in volume, such as from 5 to 40.

As an oxidizing agent, at least one oxidation-reduction enzyme such as laccases, peroxydases and 2-electron oxydoreductases (such as uricase), if necessary in the presence of their respective donor or cofactor, may also be used.

The pH of the dyeing composition (A) or of the ready-to-use composition applied to the keratin fibers [composition resulting from mixing the dye composition (A) and the oxidizing composition (B)], generally ranges for example from 4 to 12, such as from 6 to 11, and may be adjusted to the desired value by means of at least one agent chosen from acidifying and basifying agents well-known in the art of dyeing keratin fibers.

Representative basifying agents include aqueous ammonia, alkali metal carbonates, alkanolamines such as mono-, di- and triethanolamines and derivatives thereof, hydroxyalkylamines and oxyethylenated and oxypropylenated ethylenediamines, sodium and potassium hydroxide and compounds of formula (XIV):

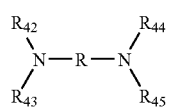
(XIV)

wherein:

R is a propylene residue optionally substituted with a group chosen from hydroxyl and $C_1$–$C_4$ alkyl groups;

$R_{42}$, $R_{43}$, $R_{44}$ and $R_{45}$, which may be identical or different, are each chosen from hydrogen, $C_1$–$C_4$ alkyl groups and $C_1$–$C_4$ hydroxyalkyl groups.

Representative acidifying agents include, classically, by way of example, organic and inorganic acids such as hydrochloric acid, orthophosphoric acid, and carboxylic acids such as tartaric acid, citric acid, lactic acid and sulfonic acids.

One dyeing method according to the invention comprises applying on dry or wet keratin fibers, such as human keratin fibers like hair, at least one ready-to-use cosmetic composition, prepared at the time of use from at least one dyeing composition (A) and at least one oxidizing composition (B), leaving said at least one ready-to-use composition on said keratin fibers for a time ranging from 1 to 60 minutes, such as from 10 to 45 minutes, rinsing said keratin fibers, optionally shampooing said keratin fibers, rinsing said keratin fibers after said optional shampooing, and drying said keratin fibers, wherein said at least one ready-to-use cosmetic composition comprises:

at least one dyeing composition (A) comprising, in a dyeing medium:
  (1) at least one oxidation dye, and
  (2) a combination comprising at least one cyclohomopolymer of dialkyldiallylammonium and at least one other particular quaternary polyammonium, and at least one oxidizing composition (B) comprising at least one oxidizing agent.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Concrete examples illustrating the invention are indicated below without however exhibiting a limiting character.

EXAMPLES

The following compositions were prepared:

| Oxidizing composition: | | |
|---|---|---|
| Fatty alcohol | | 2.3 g |
| Oxyethylenated fatty alcohol | | 0.6 g |
| Fatty amide | | 0.9 g |
| Glycerin | | 0.5 g |
| Hydrogen peroxide | | 7.5 g |
| Perfume | | qs |
| Demineralized water | qs | 100 g |

| Dyeing composition: (expressed in grams) | | |
|---|---|---|
| Mixture of C18 to C24 linear alcohols [C18/C20/C22/C24, 7/58/30/6] (NAFOL 20–22) | 3 | |
| Mixture of oxyethylenated C18 to C24 linear alcohols [C18/C20/C22/C24, 7/58/30/6] 30 EO (NAFOLOX 20–22 30EO) | 1.35 | |
| Oxyethylenated stearyl alcohol 2 EO | 4 | |
| Oxyethylenated stearyl alcohol 21 EO | 2 | |
| Oleic acid | 2.6 | |
| Glycol distearate | 2 | |
| Propylene glycol | 5 | |
| Monoisopropanolamide of copra acids | 2 | |
| Aculyn 44 sold by the company ROHM & HAAS | 1.4 | AS* |
| Crosslinked polyacrylic acid | 0.6 | |
| Quaternary polyammonium of formula (W) | 3 | AS* |
| Merquat 100 sold by the company CALGON | 0.4 | AS* |
| Reducing agents | 0.7 | |
| Seqestrants | 0.2 | |
| 1,3-Dihydroxybenzene (resorcinol) | 0.6 | |
| 1,4-Diaminobenzene | 0.5 | |
| 1-Hydroxy-3-aminobenzene | 0.1 | |
| 1-Hydroxy-2-aminobenzene | 0.05 | |
| 1-Hydroxy-4-aminobenzene | 0.09 | |
| 6-Hydroxybenzomorpholine | 0.017 | |
| 1-b-Hydroxyethyloxy-2,4-diaminobenzene, dihydrochloride | 0.039 | |
| Propylene glycol monobutyl ether | 2.5 | |
| Pure monoethanolamine | 1.06 | |
| Aqueous ammonia (containing 20.5% of ammonia). | 11.1 | |
| Water | qs | 100 |

AS* = Active Substance

The dyeing composition was mixed, at the time of use, in a plastic bowl and for 2 minutes, with the oxidizing composition given above, in an amount of 1 part of dyeing composition per 1.5 parts of oxidizing composition. The mixture obtained was applied to locks of natural grey hair which is 90% white and allowed to act for 30 minutes. The locks were then rinsed with water, they were washed with shampoo and again rinsed with water, and then dried and disentangled. The hair was then dyed in an intense light chestnut brown shade.

Results of the same type were obtained by replacing, in the above example, the quaternary polyammonium (III) with the same quantity of Miranol A15 sold by the company MIRANOL.

What is claimed is:

1. A composition for oxidation dyeing keratin fibres comprising, in an appropriate dyeing medium, (1) at least one oxidation dye, (2) at least one cyclohomopolymer of dialkyldiallylammonium comprising, as a constituent of the chain, at least one unit of structure (I):

$$\text{---}(CH_2)_t(R_{12})C \overset{(CH_2)_k}{\underset{H_2C\diagdown\diagup CH_2}{\diagdown\diagup}} C(R_{12})(CH_2)\text{---} \quad Y^-$$
$$\underset{R_{10}\ R_{11}}{N^+}$$

(I)

wherein:
  k and t, which may be identical or different, are each chosen from 0 and 1, with the proviso that the sum of k+t is equal to 1;
  $R_{12}$, which may be identical or different, are each chosen from hydrogen atoms and methyl groups;
  $R_{10}$ and $R_{11}$, which may be identical or different, are each chosen from alkyl groups comprising from 1 to 22 carbon atoms, hydroxyalkyl groups, and $C_1$–$C_4$ amidoalkyl groups;
  $R_{10}$ and $R_{11}$, together with the nitrogen atom to which they are commonly bonded, may additionally form at least one heterocyclic group;
  $Y^-$ is an anion; and (3) at least one quaternary polyammonium polymer chosen from:
  (i) polymers comprising repeating units of formula (II):

$$\text{---}\underset{R_2}{\overset{R_1}{\underset{|}{N^+}}}\text{---}(CH_2)_n\text{---}\underset{R_4}{\overset{R_3}{\underset{|}{N^+}}}\text{---}(CH_2)_p\text{---} \quad X^- \quad X^-$$

(II)

wherein:
  $R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;
  n and p, which may be identical or different, are each chosen from integers ranging from 2 to 20; and
  X– is an anion chosen from anions derived from inorganic acids and anions derived from organic acids; and (ii) polyquaternary ammonium polymers comprising repeating units of formula (V):

$$\left[ \underset{CH_3}{\overset{CH_3}{\underset{|}{N^+}}}\text{---}(CH_2)_p\text{---}\underset{H}{\overset{}{\underset{|}{N}}}\text{---}\underset{O}{\overset{}{\underset{||}{C}}}\text{---}D\text{---}\underset{H}{\overset{}{\underset{|}{N}}}\text{---}(CH_2)_p\text{---}\underset{CH_3}{\overset{CH_3}{\underset{|}{N^+}}}\text{---}(CH_2)_2\text{---}O\text{---}(CH_2)_2 \right] \quad 2X^-$$

(V)

wherein:
  p is an integer ranging from 1 to 6,
  D is chosen from direct bonds and —$(CH_2)_r$—CO— groups, wherein r is a number equal to 4 or 7, and
  $X^-$ is an anion chosen from anions derived from inorganic acids and anions derived from organic acids.

2. A composition according to claim 1, wherein said keratin fibers are chosen from human keratin fibers.

3. A composition according to claim 2, wherein said human keratin fibers are chosen from human hair.

4. A composition according to claim 1, wherein in said formula (I) said $R_{12}$ is hydrogen, said $R_{10}$ and $R_{11}$ are methyl groups, and $Y^-$ is chloride.

5. A composition according to claim 1, wherein in said formula (II) said $R_1$, $R_2$, $R_3$ and $R_4$, which may be identical or different, are each chosen from methyl and ethyl groups, and $X^-$ is a halogen atom.

6. A composition according to claim 5, wherein in said formula (II) said $R_1$, $R_2$, $R_3$ and $R_4$ are methyl groups, n=3, p=6 and $X^-$ is chloride.

7. A composition according to claim 5, wherein in said formula (II) said $R_1$, and $R_2$ are methyl groups, $R_3$ and $R_4$ are ethyl groups, n=p=3 and $X^-$ is bromide.

8. A composition according to claim 1, wherein said D of said formula (V) is a direct bond and $X^-$ is chloride.

9. A composition according to claim 1, wherein said at least one cyclohomopolymer of dialkyldiallylammonium with units of formula (I) is present in an amount ranging from 0.05% to 5% by weight relative to the total weight of the composition.

10. A composition according to claim 9, wherein said at least one cyclohomopolymer of dialkyldiallylammonium with units of formula (I) is present in an amount ranging from 0.1% to 3% by weight relative to the total weight of the composition.

11. A composition according to claim 4, wherein said at least one cyclohomopolymer of dialkyldiallylammonium with units of formula (I) is present in an amount ranging from 0.05% to 5% by weight relative to the total weight of the composition.

12. A composition according to claim 11, wherein said at least one cyclohomopolymer of dialkyldiallylammonium with units of formula (I) is present in an amount ranging from 0.1% to 3% by weight relative to the total weight of the composition.

13. A composition according to claim 1, wherein said at least one quaternary polyammonium polymer is present in an amount ranging from 0.05% to 10% by weight relative to the total weight of the composition.

14. A composition according to claim 13, wherein said at least one quaternary polyammonium polymer is present in an amount ranging from 0.2% to 5% by weight relative to the total weight of the composition.

15. A composition according to claim 1, wherein the weight ratio of said at least one quaternary polyammonium polymer to said at least one cyclohomopolymer of dialkyldiallylammonium ranges from 0.1:1 to 50:1.

16. A composition according to claim 15, wherein said weight ratio of said at least one quaternary polyammonium polymer to said at least one cyclohomopolymer of dialkyldiallylammonium ranges from 1:1 to 10:1.

17. A composition according to claim 1, wherein said at least one oxidation dye is chosen from oxidation bases, oxidation couplers, and their acid addition salts.

18. A composition according to claim 1, wherein said at least one oxidation dye is chosen from oxidation bases.

19. A composition according to claim 18, wherein said oxidation bases are chosen from ortho- and para-phenylenediamines, double bases, ortho- and para-aminophenols, heterocyclic bases, and acid addition salts of any of the foregoing.

20. A composition according to claim 19, wherein said para-phenylenediamines are chosen from compounds of formula (VI):

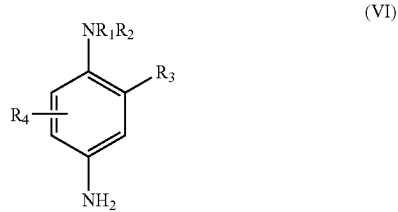

wherein:
R$_1$ is chosen from hydrogen, C$_1$–C$_4$ alkyl groups, monohydroxy(C$_1$–C$_4$ alkyl) groups, polyhydroxy(C$_2$–C$_4$ alkyl) groups, (C$_1$–C$_4$)alkoxy(C$_1$–C$_4$)alkyl groups, phenyl groups, 4'-aminophenyl groups, and C$_1$–C$_4$ alkyl groups substituted with at least one group chosen from nitrogen-containing groups, R$_2$ is chosen from hydrogen, C$_1$–C$_4$ alkyl groups, monohydroxy(C$_1$–C$_4$ alkyl) groups, polyhydroxy(C$_2$–C$_4$ alkyl) groups, (C$_1$–C$_4$)alkoxy(C$_1$–C$_4$)alkyl groups, and C$_1$–C$_4$ alkyl groups substituted with a nitrogen-containing group;

R$_1$ and R$_2$ may also form, together with the nitrogen atom to which they are bonded, a 5- or 6-membered nitrogen-containing heterocycle ring, optionally substituted with at least one group chosen from alkyl groups, hydroxyl groups and ureido groups;

R$_3$ is chosen from hydrogen, halogens, C$_1$–C$_4$ alkyl groups, sulfo groups, carboxyl groups, monohydroxy (C$_1$–C$_4$ alkyl) groups, hydroxy(C$_1$–C$_4$ alkyoxy) groups, acetylamino(C$_1$–C$_4$ alkoxy) groups, mesylamino (C$_1$–C$_4$ alkoxy) groups, and carbamoylamino(C$_1$–C$_4$ alkoxy) groups; and R$_4$ is chosen from hydrogen, halogens, and C$_1$–C$_4$ alkyl groups.

21. A composition according to claim 20, wherein said R$_3$ is chlorine.

22. A composition according to claim 19, wherein said double bases are chosen from compounds of formula (VII):

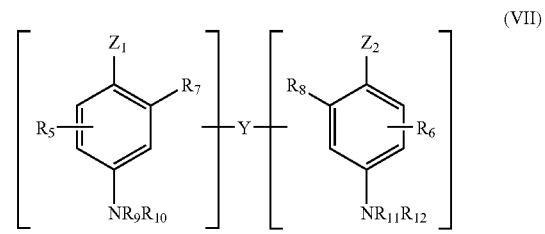

wherein:
Z$_1$ and Z$_2$, which may be identical or different, are each chosen from hydroxyl groups, and —NH$_2$ groups, optionally substituted with a group chosen from C$_1$–C$_4$ alkyl groups, and linkers Y;

linker Y is chosen from linear and branched, divalent alkylene groups comprising from 1 to 14 carbon atoms, optionally interrupted by, or optionally terminating with, at least one entity chosen from nitrogen-containing groups and heteroatoms, and optionally substituted with at least one group chosen from hydroxyl groups, and C$_1$–C$_6$ alkoxy groups;

R$_5$ and R$_6$, which may be identical or different, are each chosen from hydrogen, halogens, C$_1$–C$_4$ alkyl groups, monohydroxy(C$_1$–C$_4$ alkyl) groups, polyhydroxy (C$_2$–C$_4$ alkyl) groups, amino(C$_1$–C$_4$ alkyl) groups, and linkers Y; and R$_7$, R$_8$, R$_9$, R$_{10}$, R$_{11}$ and R$_{12}$, which may be identical or different, are each chosen from hydrogen, linkers Y, and C$_1$–C$_4$ alkyl groups;

provided that said compounds of formula (VII) comprise only one linker Y per molecule.

23. A composition according to claim 22, wherein said heteroatoms are chosen from oxygen, sulfur, and nitrogen.

24. A composition according to claim 20, wherein said nitrogen-containing groups are chosen from amino, mono (C$_1$–C$_4$)alkylamino, (C$_1$–C$_4$)dialkylamino, (C$_1$–C$_4$)trialkylamino, monohydroxy(C$_1$–C$_4$)alkylamino, imidazolinium and ammonium radicals.

25. A composition according to claim 22, wherein said nitrogen-containing groups are chosen from amino, mono ($C_1$–$C_4$)alkylamino, ($C_1$–$C_4$)dialkylamino, ($C_1$–$C_4$)trialkylamino, monohydroxy($C_1$–$C_4$)alkylamino, imidazolinium and ammonium radicals.

26. A composition according to claim 19, wherein said para-aminophenols are chosen from compounds of formula (VIII):

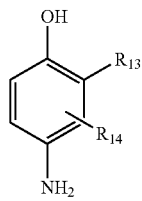

wherein:
$R_{13}$ is chosen from hydrogen, halogens, $C_1$–$C_4$ alkyl groups, monohydroxy($C_1$–$C_4$ alkyl) groups, ($C_1$–$C_4$) alkoxy($C_1$–$C_4$)alkyl groups, amino($C_1$–$C_4$ alkyl), and hydroxy($C_1$–$C_4$)alkylamino($C_1$–$C_4$ alkyl) groups;
$R_{14}$ is chosen from hydrogen, halogens, $C_1$–$C_4$ alkyl groups, monohydroxy($C_1$–$C_4$ alkyl) groups, polyhydroxy($C_2$–$C_4$ alkyl) groups, amino($C_1$–$C_4$ alkyl) groups, cyano($C_1$–$C_4$ alkyl) groups, and ($C_1$–$C_4$) alkoxy($C_1$–$C_4$)alkyl groups.

27. A composition according to claim 26, wherein said halogens are fluorine.

28. A composition according to claim 19, wherein said heterocyclic bases are chosen from pyridine derivatives, pyrimidine derivatives, pyrazolopyrimidine derivatives, and pyrazole derivatives.

29. A composition according to claim 18, wherein said oxidation bases are present in an amount ranging from 0.0005% to 12% by weight relative to the total weight of the composition.

30. A composition according to claim 17, wherein said oxidation couplers are chosen from meta-phenylenediamines, meta-aminophenols, meta-diphenols, heterocyclic couplers, and their acid addition salts.

31. A composition according to claim 17, wherein said oxidation couplers are present in an amount ranging from 0.0001% to 10% by weight relative to the total weight of the composition.

32. A composition according to claim 17, wherein said acid addition salts are chosen from hydrochlorides, hydrobromides, sulfates, tartrates, lactates, and acetates.

33. A composition according to claim 1 further comprising at least one direct dye.

34. A composition according to claim 1 further comprising at least one reducing agent.

35. A composition according to claim 34, wherein said at least one reducing agent is present in an amount ranging from 0.05% to 3% by weight relative to the total weight of the composition.

36. A composition according to claim 1 further comprising at least one fatty alcohol.

37. A composition according to claim 36, wherein said at least one fatty alcohol is present in an amount ranging from 0.001% to 20% by weight relative to the total weight of the composition.

38. A ready-to-use cosmetic composition for oxidation dyeing keratin fibers, wherein said ready-to-use cosmetic composition is obtained by including at least one dyeing composition (A) in a dyeing medium, comprising:

at least one oxidation dye,
at least one cyclohomopolymer of dialkyldiallylammonium comprising, as a constituent of the chain, at least one unit of structure (I):

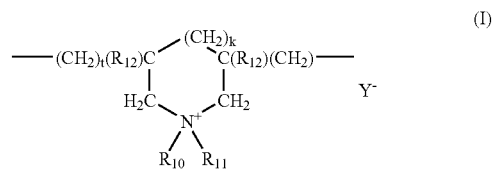

wherein:
k and t, which may be identical or different, are each chosen from 0 and 1, with the proviso that the sum of k+t is equal to 1;
$R_{12}$, which may be identical or different, are each chosen from hydrogen atoms and methyl groups;
$R_{10}$ and $R_{11}$, which may be identical or different, are each chosen from alkyl groups comprising from 1 to 22 carbon atoms, hydroxyalkyl groups, and $C_1$–$C_4$ amidoalkyl groups;
$R_{10}$ and $R_{11}$, together with the nitrogen atom to which they are commonly bonded, may additionally form at least one heterocyclic group;
$Y^-$ is an anion; and
at least one quaternary polyammonium polymer chosen from:

(i) polymers comprising repeating units of formula (II):

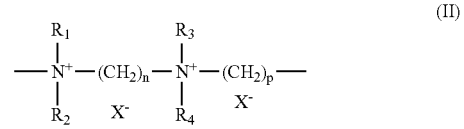

wherein:
$R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;
n and p, which may be identical or different, are each chosen from integers ranging from 2 to 20; and
$X^-$ is an anion chosen from anions derived from inorganic acids and anions derived from organic acids; and (ii) polyquaternary ammonium polymers comprising repeating units of formula (V):

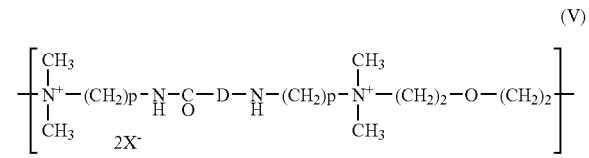

wherein:
p is an integer ranging from 1 to 6,
D is chosen from direct bonds and —$(CH_2)_r$—CO— groups, wherein r is a number equal to 4 or 7, and X⁻ is an anion chosen from anions derived from inorganic acids and anions derived from organic acids, with at least one oxidizing composition (B) comprising at least one oxidizing agent.

39. A composition according to claim 38, wherein said at least one oxidizing agent is chosen from hydrogen peroxide, urea peroxide, alkali metal bromates, alkali metal ferricyanides, persalts, and oxidation-reduction enzymes.

40. A composition according to claim 39, wherein said oxidation-reduction enzymes are chosen from laccases, peroxidases, and oxidoreductases comprising 2 electrons.

41. A composition according to claim 40, wherein said at least one oxidizing agent is hydrogen peroxide.

42. A composition according to claim 41, wherein said hydrogen peroxide is present in an oxygenated water solution comprising a titre ranging from 1 to 40 in volume.

43. A composition according to claim 1, wherein said composition possesses a pH ranging from 4 to 12.

44. A composition according to claim 38, wherein said keratin fibers are chosen from human keratin fibers.

45. A composition according to claim 44, wherein said human keratin fibers are chosen from human hair.

46. A cosmetic composition according to claim 38 further comprising at least one thickening polymer comprising at least one fatty chain in said at least one dyeing composition (A), in said at least one oxidizing composition (B), or in said at least one dyeing composition (A) and said at least one oxidizing composition (B).

47. A composition according to claim 46, wherein said at least one thickening polymer comprising at least one fatty chain is chosen from nonionic thickening polymers.

48. A composition according to claim 46, wherein said at least one thickening polymer comprising at least one fatty chain is present in an amount ranging from 0.01% to 10% by weight relative to the total weight of the composition.

49. A composition according to claim 48, wherein said at least one thickening polymer comprising at least one fatty chain is present in an amount ranging from 0.1% to 5% by weight relative to the total weight of the composition.

50. A composition according to claim 38 further comprising at least one surfactant chosen from anionic, cationic, nonionic and amphoteric surfactants, wherein said at least one surfactant is present in said at least one dyeing composition (A), in said at least one oxidizing composition (B), or in said at least one dyeing composition (A) and said at least one one compostion (B).

51. A composition according to claim 50, wherein said at least one surfactant is present in an amount ranging from 0.01% to 40% by weight relative to the total weight of the composition.

52. A composition according to claim 51, wherein said at least one surfactant is present in an amount ranging from 0.1% to 30% by weight relative to the total weight of the composition.

53. A composition according to claim 38 further comprising at least one thickening agent chosen from cellulose derivatives, guar derivatives, gums of microbial origin, and synthetic thickeners which do not possess a fatty chain, wherein said at least one thickening agent is present in said at least one dyeing composition (A), in said at least one oxidizing composition (B), or in said at least one dyeing composition (A) and said at least one oxidizing composition (B).

54. A composition according to claim 53, wherein said at least one thickening agent is present in an amount ranging from 0.01% to 10% by weight relative to the total weight of the composition.

55. A method for oxidation dyeing keratin fibers comprising:
(a) applying to said keratin fibers at least one dyeing composition (A) comprising, in a dyeing medium:
at least one oxidation dye, and
a combination comprising:
(I) at least one cyclohomopolymer of dialkyldiallylammonium comprising, as a constituent of the chain, at least one unit of structure (I):

$$\text{---}(CH_2)_t(R_{12})C \overset{(CH_2)_k}{\underset{H_2C\underset{\underset{R_{10}}{\diagup}\underset{R_{11}}{\diagdown}}{N^+}CH_2}{\diagdown}} C(R_{12})(CH_2)\text{---} \quad Y^- \tag{I}$$

wherein:
k and t, which may be identical or different, are each chosen from 0 and 1, with the proviso that the sum of k+t is equal to 1;
$R_{12}$, which may be identical or different, are each chosen from hydrogen atoms and methyl groups;
$R_{10}$ and $R_{11}$, which may be identical or different, are each chosen from alkyl groups comprising from 1 to 22 carbon atoms, hydroxyalkyl groups, and $C_1$–$C_4$ amidoalkyl groups;
$R_{10}$ and $R_{11}$, together with the nitrogen atom to which they are commonly bonded, may additionally form at least one heterocyclic group;
Y⁻ is an anion; and
(II) at least one quaternary polyammonium polymer chosen from:
(i) polymers comprising repeating units of formula (II):

$$\text{---}\underset{R_2}{\overset{R_1}{\underset{|}{\overset{|}{N^+}}}}\text{---}(CH_2)_n\text{---}\underset{R_4}{\overset{R_3}{\underset{|}{\overset{|}{N^+}}}}\text{---}(CH_2)_p\text{---} \quad X^- \quad X^- \tag{II}$$

wherein:
$R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;
n and p, which may be identical or different, are each chosen from integers ranging from 2 to 20; and
X⁻ is an anion chosen from anions derived from inorganic acids and anions derived from organic acids; and
(ii) polyquaternary ammonium polymers comprising repeating units of formula (V):

$$\left[\underset{CH_3}{\overset{CH_3}{\underset{|}{\overset{|}{N^+}}}}\text{---}(CH_2)_p\text{-}\underset{H}{\overset{}{N}}\text{-}\underset{O}{\overset{}{C}}\text{---}D\text{---}\underset{H}{\overset{}{N}}\text{---}(CH_2)_p\text{---}\underset{CH_3}{\overset{CH_3}{\underset{|}{\overset{|}{N^+}}}}\text{---}(CH_2)_2\text{-}O\text{---}(CH_2)_2\right] \quad 2X^- \tag{V}$$

wherein:
p is an integer ranging from 1 to 6,
D is chosen from direct bonds and —$(CH_2)_r$—CO— groups, wherein r is a number equal to 4 or 7, and X⁻ is an anion chosen from anions derived from inorganic acids and anions derived from organic acids, and (b) developing the color with the aid of at least one oxidizing composition (B) comprising at least one oxidizing agent, wherein said at least one oxidizing composition (B) is combined at the time of use with said at least one dyeing composition (A) or said at least one oxidizing composition (B) is applied sequentially to said at least one dyeing composition (A) without intermediate rinsing.

56. A method according to claim 55, wherein said keratin fibers are chosen from human keratin fibers.

57. A method according to claim 56, wherein said human keratin fibers are human hair.

58. A method for oxidation dyeing keratin fibers comprising:

(a) applying to said keratin fibers at least one dyeing composition (A) comprising, in a dyeing medium:
at least one oxidation dye, and
a combination comprising:
(I) at least one cyclohomopolymer of dialkyldiallylammonium comprising, as a constituent of the chain, at least one unit of structure (I):

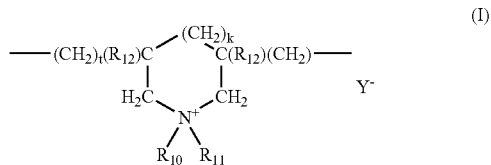

wherein:
k and t, which may be identical or different, are each chosen from 0 and 1, with the proviso that the sum of k+t is equal to 1;
$R_{12}$, which may be identical or different, are each chosen from hydrogen atoms and methyl groups;
$R_{10}$ and $R_{11}$, which may be identical or different, are each chosen from alkyl groups comprising from 1 to 22 carbon atoms, hydroxyalkyl groups, and $C_1$–$C_4$ amidoalkyl groups;
$R_{10}$ and $R_{11}$, together with the nitrogen atom to which they are commonly bonded, may additionally form at least one heterocyclic group;
Y⁻ is an anion; and
(II) at least one quaternary polyammonium polymer chosen from:
(i) polymers comprising repeating units of formula (II):

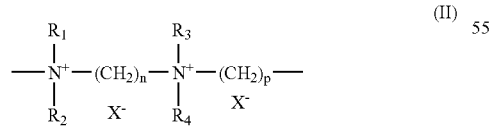

wherein:
$R_1$, $R_2$, $R_3$ and $R^4$, which may be identical or different, are each chosen from alkyl groups comprising from 1 to 4 carbon atoms and hydroxyalkyl groups comprising from 1 to 4 carbon atoms;
n and p, which may be identical or different, are each chosen from integers ranging from 2 to 20; and X⁻ is an anion chosen from anions derived from inorganic acids and anions derived from organic acids; and (ii) polyquaternary ammonium polymers comprising repeating units of formula (V):

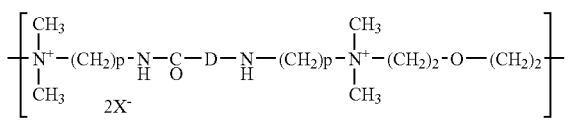

wherein:
p is an integer ranging from 1 to 6,
D is chosen from direct bonds and —$(CH_2)_r$—CO— groups, wherein r is a number equal to 4 or 7, and
X⁻ is an anion chosen from anions derived from inorganic acids and anions derived from organic acids, and (b) developing the color with the aid of at least one oxidizing composition (B) comprising:
at least one oxidizing agent, and
a combination comprising at least one cyclohomopolymer of dialkyldiallylammonium as defined above and at least one other quaternary polyammonium as defined above,
wherein said at least one oxidizing composition (B) is combined at the time of use with said at least one dyeing composition (A) or said at least one oxidizing composition (B) is applied sequentially to said at least one dyeing composition (A) without intermediate rinsing.

59. A method according to claim 58, wherein said keratin fibers are chosen from human keratin fibers.

60. A method according to claim 59, wherein said human keratin fibers are human hair.

61. A method for oxidation dyeing keratin fibers comprising:
applying to said keratin fibers at least one dyeing composition (A) comprising, in a dyeing medium, at least one oxidation dye,
developing the color with the aid of at least one oxidizing composition (B) comprising at least one oxidizing agent,
wherein said oxidizing composition (B) comprises a combination comprising:
(I) at least one cyclohomopolymer of dialkyldiallylammonium comprising, as a constituent of the chain, at least one unit of structure (I):

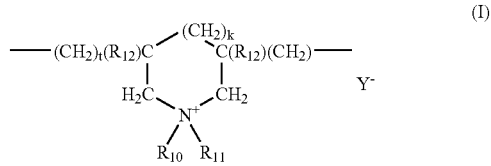

wherein:
k and t, which may be identical or different, are each chosen from 0 and 1, with the proviso that the sum of k+t is equal to 1;
$R_{12}$, which may be identical or different, are each chosen from hydrogen atoms and methyl groups;

$R_{10}$ and $R_{11}$, which may be identical or different, are each chosen from alkyl groups comprising from 1 to 22 carbon atoms, hydroxyalkyl groups, and $C_1$–$C_4$ amidoalkyl groups;

$R_{10}$ and $R_{11}$, together with the nitrogen atom to which they are commonly bonded, may additionally form at least one heterocyclic group;

$Y^-$ is an anion; and (II) at least one quaternary polyammonium polymer chosen from:

(i) polymers comprising repeating units of formula (II):

$$—\underset{\underset{R_2}{|}}{\overset{\overset{R_1}{|}}{N^+}}—(CH_2)_n—\underset{\underset{R_4}{|}}{\overset{\overset{R_3}{|}}{N^+}}—(CH_2)_p— \quad X^- \quad X^- \tag{II}$$

wherein:

$R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;

n and p, which may be identical or different, are each chosen from integers ranging from 2 to 20; and $X^-$ is an anion chosen from anions derived from inorganic acids and anions derived from organic acids; and (ii) polyquaternary ammonium polymers comprising repeating units of formula (V):

$$\left[\underset{\underset{CH_3}{|}}{\overset{\overset{CH_3}{|}}{N^+}}—(CH_2)_p—\underset{H}{N}—\underset{O}{C}—D—\underset{H}{N}—(CH_2)_p—\underset{\underset{CH_3}{|}}{\overset{\overset{CH_3}{|}}{N^+}}—(CH_2)_2—O—(CH_2)_2\right] \quad 2X^- \tag{V}$$

wherein:

p is an integer ranging from 1 to 6,

D is chosen from direct bonds and —$(CH_2)_r$—CO— groups, wherein r is a number equal to 4 or 7, and $X^-$ is an anion chosen from anions derived from inorganic acids and anions derived from organic acids, wherein said at least one oxidizing composition (B) is combined at the time of use with said at least one dyeing composition (A) or wherein said at least one oxidizing composition (B) is applied sequentially to said at least one dyeing composition (A) without intermediate rinsing.

62. A method according to claim 61, wherein said keratin fibers are chosen from human keratin fibers.

63. A method according to claim 62, wherein said human keratin fibers are human hair.

64. A kit for dyeing keratin fibers comprising at least two compartments, wherein:

a first compartment comprises at least one oxidation dye and a combination comprising:

(I) at least one cyclohomopolymer of dialkyldiallylammonium comprising, as a constituent of the chain, at least one unit of structure (I):

$$—(CH_2)_t(R_{12})C\underset{\underset{N^+}{\underset{R_{10} \ R_{11}}{|}}}{\overset{(CH_2)_k}{\diagup\!\!\!\diagdown}}C(R_{12})(CH_2)— \quad Y^- \tag{I}$$

(with $H_2C$ and $CH_2$ completing the ring)

wherein:

k and t, which may be identical or different, are each chosen from 0 and 1, with the proviso that the sum of k+t is equal to 1;

$R_{12}$, which may be identical or different, are each chosen from hydrogen atoms and methyl groups;

$R_{10}$ and $R_{11}$, which may be identical or different, are each chosen from alkyl groups comprising from 1 to 22 carbon atoms, hydroxyalkyl groups, and $C_1$–$C_4$ amidoalkyl groups;

$R_{10}$ and $R_{11}$, together with the nitrogen atom to which they are commonly bonded, may additionally form at least one heterocyclic group;

$Y^-$ is an anion; and (II) at least one quaternary polyammonium polymer chosen from:

(i) polymers comprising repeating units of formula (II):

$$—\underset{\underset{R_2}{|}}{\overset{\overset{R_1}{|}}{N^+}}—(CH_2)_n—\underset{\underset{R_4}{|}}{\overset{\overset{R_3}{|}}{N^+}}—(CH_2)_p— \quad X^- \quad X^- \tag{II}$$

wherein:

$R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;

n and p, which may be identical or different, are each chosen from integers ranging from 2 to 20; and $X^-$ is an anion chosen from anions derived from inorganic acids and anions derived from organic acids; and (ii) polyquaternary ammonium polymers comprising repeating units of formula (V):

$$\left[\underset{\underset{CH_3}{|}}{\overset{\overset{CH_3}{|}}{N^+}}—(CH_2)_p—\underset{H}{N}—\underset{O}{C}—D—\underset{H}{N}—(CH_2)_p—\underset{\underset{CH_3}{|}}{\overset{\overset{CH_3}{|}}{N^+}}—(CH_2)_2—O—(CH_2)_2\right] \quad 2X^- \tag{V}$$

wherein:

p is an integer ranging from 1 to 6,

D is chosen from direct bonds and —$(CH_2)_r$—CO— groups, wherein r is a number equal to 4 or 7, and $X^-$ is an anion chosen from anions derived from inorganic acids and anions derived from organic acids, and a second compartment comprises at least one oxidizing agent.

65. A kit according to claim 64, wherein said keratin fibers are chosen from human keratin fibers.

66. A kit according to claim 65, wherein said human keratin fibers are human hair.

67. A composition according to claim 36, wherein said at least one fatty alcohol is chosen from linear and branched, saturated and unsaturated fatty alcohols.

68. A composition according to claim 1, wherein in said $R_{10}$ and $R_{11}$ said alkyl radical of said hydroxyalkyl groups comprises from 1 to 5 carbon atoms.

69. A composition according to claim 38, wherein in said $R_{10}$ and $R_{11}$ said alkyl radical of said hydroxyalkyl groups comprises from 1 to 5 carbon atoms.

70. A method according to claim 55, wherein in said $R_{10}$ and $R_{11}$ said alkyl radical of said hydroxyalkyl groups comprises from 1 to 5 carbon atoms.

71. A method according to claim 58, wherein in said $R_{10}$ and $R_{11}$ said alkyl radical of said hydroxyalkyl groups comprises from 1 to 5 carbon atoms.

72. A method according to claim 61, wherein in said $R_{10}$ and $R_{11}$ said alkyl radical of said hydroxyalkyl groups comprises from 1 to 5 carbon atoms.

73. A kit according to claim 64, wherein in said $R_{10}$ and $R_{11}$ said alkyl radical of said hydroxyalkyl groups comprises from 1 to 5 carbon atoms.

74. A method for oxidation dyeing keratin fibers comprising:
   (a) applying to said keratin fibers at least one dyeing composition (A) comprising, in a dyeing medium:
      at least one oxidation dye, and
   (b) developing the color with the aid of at least one oxidizing composition (B) comprising at least one oxidizing agent, wherein said at least one oxidizing composition (B) is combined at the time of use with said at least one dyeing composition (A) or said at least one oxidizing composition (B) is applied sequentially to said at least one dyeing composition (A) without intermediate rinsing, wherein:
      (I) said at least one dyeing composition (A) comprises:
         at least one cyclohomopolymer of dialkyldiallylammonium comprising, as a constituent of the chain, at least one unit of structure (I):

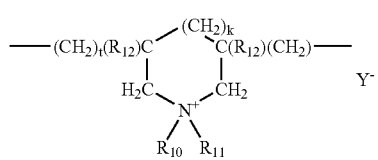

wherein:
   k and t, which may be identical or different, are each chosen from 0 and 1, with the proviso that the sum of k+t is equal to 1;
   $R_{12}$, which may be identical or different, are each chosen from hydrogen atoms and methyl groups;
   $R_{10}$ and $R_{11}$, which may be identical or different, are each chosen from alkyl groups comprising from 1 to 22 carbon atoms, hydroxyalkyl groups, and $C_1$–$C_4$ amidoalkyl groups;

$R_{10}$ and $R_{11}$, together with the nitrogen atom to which they are commonly bonded, may additionally form at least one heterocyclic group;
$Y^-$ is an anion; and wherein:
(II) said at least one oxidizing composition (B) comprises:
at least one quaternary polyammonium polymer chosen from:
   (i) polymers comprising repeating units of formula (II):

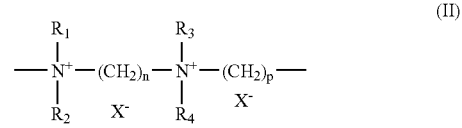

wherein:
   $R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;
   n and p, which may be identical or different, are each chosen from integers ranging from 2 to 20; and
   $X^-$ is an anion chosen from anions derived from inorganic acids and anions derived from organic acids; and
   (ii) polyquaternary ammonium polymers comprising repeating units of formula (V):

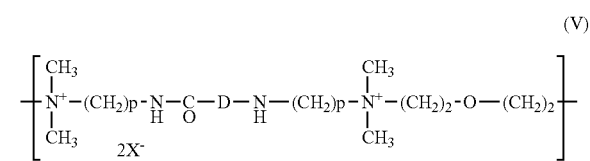

wherein:
   p is an integer ranging from 1 to 6,
   D is chosen from direct bonds and —$(CH_2)_r$—CO— groups, wherein r is a number equal to 4 or 7, and
   $X^-$ is an anion chosen from anions derived from inorganic acids and anions derived from organic acids.

75. A method according to claim 74, wherein said keratin fibers are chosen from human keratin fibers.

76. A method according to claim 75, wherein said human keratin fibers are human hair.

77. A method for oxidation dyeing keratin fibers comprising:
   (a) applying to said keratin fibers at least one dyeing composition (A) comprising, in a dyeing medium:
      at least one oxidation dye, and
   (b) developing the color with the aid of at least one oxidizing composition (B) comprising at least one oxidizing agent, wherein said at least one oxidizing composition (B) is combined at the time of use with said at least one dyeing composition (A) or said at least one oxidizing composition (B) is applied sequentially to said at least one dyeing composition (A) without intermediate rinsing, wherein:
      (I) said at least one oxidizing composition (B) comprises:
         at least one cyclohomopolymer of dialkyldiallylammonium comprising, as a constituent of the chain, at least one unit of structure (I):

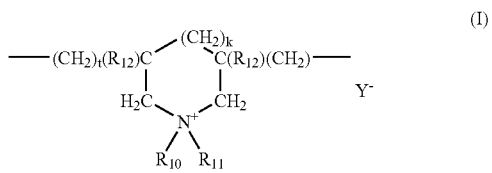

wherein:
- k and t, which may be identical or different, are each chosen from 0 and 1, with the proviso that the sum of k+t is equal to 1;
- $R_{12}$, which may be identical or different, are each chosen from hydrogen atoms and methyl groups;
- $R_{10}$ and $R_{11}$, which may be identical or different, are each chosen from alkyl groups comprising from 1 to 22 carbon atoms, hydroxyalkyl groups, and $C_1$–$C_4$ amidoalkyl groups;
- $R_{10}$ and $R_{11}$, together with the nitrogen atom to which they are commonly bonded, may additionally form at least one heterocyclic group;
- $Y^-$ is an anion; and wherein:

(II) said at least one dyeing composition (A) comprises:
at least one quaternary polyammonium polymer chosen from:
  (i) polymers comprising repeating units of formula (II):

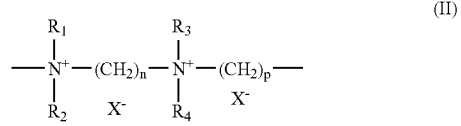

wherein:
- $R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;
- n and p, which may be identical or different, are each chosen from integers ranging from 2 to 20; and
- $X^-$ is an anion chosen from anions derived from inorganic acids and anions derived from organic acids; and
  (ii) polyquaternary ammonium polymers comprising repeating units of formula (V):

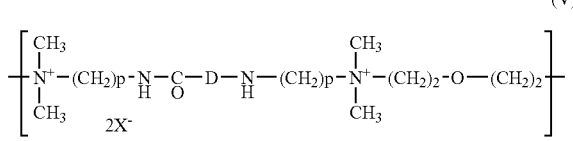

wherein:
- p is an integer ranging from 1 to 6,
- D is chosen from direct bonds and —$(CH_2)_r$—CO— groups, wherein r is a number equal to 4 or 7, and
- $X^-$ is an anion chosen from anions derived from inorganic acids and anions derived from organic acids.

78. A method according to claim 77, wherein said keratin fibers are chosen from human keratin fibers.

79. A method according to claim 78, wherein said human keratin fibers are human hair.

80. A kit for dyeing keratin fibers comprising at least two compartments, wherein:
- a first compartment comprises at least one oxidation dye and
- a second compartment comprises at least one oxidizing agent and a combination comprising:

(I) at least one cyclohomopolymer of dialkyldiallylammonium comprising, as a constituent of the chain, at least one unit of structure (I):

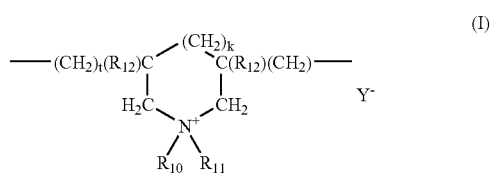

wherein:
- k and t, which may be identical or different, are each chosen from 0 and 1, with the proviso that the sum of k+t is equal to 1;
- $R_{12}$, which may be identical or different, are each chosen from hydrogen atoms and methyl groups;
- $R_{10}$ and $R_{11}$, which may be identical or different, are each chosen from alkyl groups comprising from 1 to 22 carbon atoms, hydroxyalkyl groups, and $C_1$–$C_4$ amidoalkyl groups;
- $R_{10}$ and $R_{11}$, together with the nitrogen atom to which they are commonly bonded, may additionally form at least one heterocyclic group;
- $Y^-$ is an anion; and (II) at least one quaternary polyammonium polymer chosen from:
  (i) polymers comprising repeating units of formula (II):

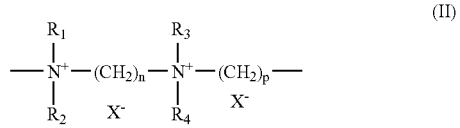

wherein:
- $R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;
- n and p, which may be identical or different, are each chosen from integers ranging from 2 to 20; and
- $X^-$ is an anion chosen from anions derived from inorganic acids and anions derived from organic acids; and
  (ii) polyquaternary ammonium polymers comprising repeating units of formula (V):

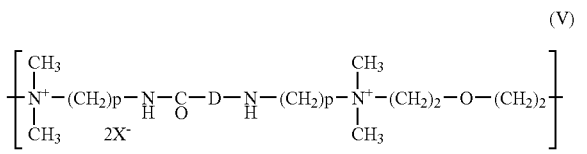

(V)

wherein:
p is an integer ranging from 1 to 6,
D is chosen from direct bonds and —(CH$_2$)$_r$—CO— groups, wherein r is a number equal to 4 or 7, and
X$^-$ is an anion chosen from anions derived from inorganic acids and anions derived from organic acids.

81. A kit according to claim 80, wherein said keratin fibers are chosen from human keratin fibers.

82. A kit according to claim 81, wherein said human keratin fibers are human hair.

83. A kit for dyeing keratin fibers comprising at least two compartments, wherein:
a first compartment comprises at least one oxidation dye and a combination comprising:
(I) at least one cyclohomopolymer of dialkyldiallylammonium comprising, as a constituent of the chain, at least one unit of structure (I):

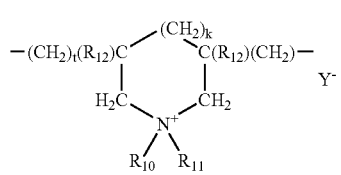

(I)

wherein:
k and t, which may be identical or different, are each chosen from 0 and 1, with the proviso that the sum of k+t is equal to 1;
R$_{12}$, which may be identical or different, are each chosen from hydrogen atoms and methyl groups;
R$_{10}$ and R$_{11}$, which may be identical or different, are each chosen from alkyl groups comprising from 1 to 22 carbon atoms, hydroxyalkyl groups, and C$_1$–C$_4$ amidoalkyl groups;
R$_{10}$ and R$_{11}$, together with the nitrogen atom to which they are commonly bonded, may additionally form at least one heterocyclic group;
Y$^-$ is an anion; and
(II) at least one quaternary polyammonium polymer chosen from:
(i) polymers comprising repeating units of formula (II):

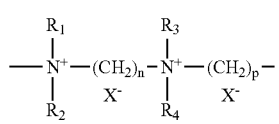

(II)

wherein:
R$_1$, R$_2$, R$_3$ and R$_4$, which may be identical or different, are each chosen from alkyl groups comprising from 1 to 4 carbon atoms and hydroxyalkyl groups comprising from 1 to 4 carbon atoms;

n and p, which may be identical or different, are each chosen from integers ranging from 2 to 20; and
X$^-$ is an anion chosen from anions derived from inorganic acids and anions derived from organic acids; and
(ii) polyquaternary ammonium polymers comprising repeating units of formula (V):

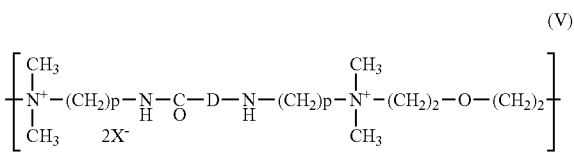

(V)

wherein:
p is an integer ranging from 1 to 6,
D is chosen from direct bonds and —(CH$_2$)$_r$—CO— groups, wherein r is a number equal to 4 or 7, and
X$^-$ is an anion chosen from anions derived from inorganic acids and anions derived from organic acids, and
a second compartment comprises at least one oxidizing agent and a combination comprising at least one cyclohomopolymer of dialkyldiallylammonium as defined above and at least one other quaternary polyammonium polymer as defined above.

84. A kit according to claim 83, wherein said keratin fibers are chosen from human keratin fibers.

85. A kit according to claim 84, wherein said human keratin fibers are human hair.

86. A kit for dyeing keratin fibers comprising at least two compartments, wherein:
a first compartment comprises at least one oxidation dye and at least one cyclohomopolymer of dialkyldiallylammonium comprising, as a constituent of the chain, at least one unit of structure (I):

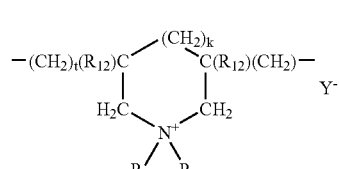

(I)

wherein:
k and t, which may be identical or different, are each chosen from 0 and 1, with the proviso that the sum of k+t is equal to 1;
R$_{12}$, which may be identical or different, are each chosen from hydrogen atoms and methyl groups;
R$_{10}$ and R$_{11}$, which may be identical or different, are each chosen from alkyl groups comprising from 1 to 22 carbon atoms, hydroxyalkyl groups, and C$_1$–C$_4$ amidoalkyl groups;
R$_{10}$ and R$_{11}$, together with the nitrogen atom to which they are commonly bonded, may additionally form at least one heterocyclic group;
Y$^-$ is an anion, and wherein:
a second compartment comprises at least one oxidizing agent and at least one quaternary polyammonium polymer chosen from:

(i) polymers comprising repeating units of formula (II):

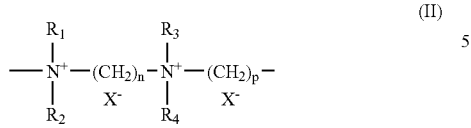

wherein:
R₁, R₂, R₃ and R₄, which may be identical or different, are each chosen from alkyl groups comprising from 1 to 4 carbon atoms and hydroxyalkyl groups comprising from 1 to 4 carbon atoms;
n and p, which may be identical or different, are each chosen from integers ranging from 2 to 20; and
X⁻ is an anion chosen from anions derived from inorganic acids and anions derived from organic acids; and
(ii) polyquaternary ammonium polymers comprising repeating units of formula (V):

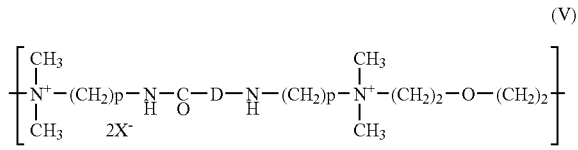

wherein:
p is an integer ranging from 1 to 6,
D is chosen from direct bonds and —(CH₂)ᵣ—CO— groups, wherein r is a number equal to 4 or 7, and
X⁻ is an anion chosen from anions derived from inorganic acids and anions derived from organic acids.

87. A kit according to claim 86, wherein said keratin fibers are chosen from human keratin fibers.

88. A kit according to claim 87, wherein said human keratin fibers are human hair.

89. A kit for dyeing keratin fibers comprising at least two compartments, wherein:
a first compartment comprises at least one oxidation dye and at least one quaternary polyammonium polymer chosen from:
(i) polymers comprising repeating units of formula (II):

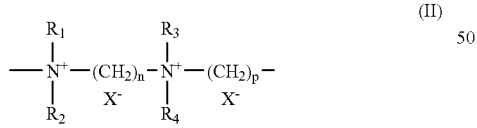

wherein:
R₁, R₂, R₃ and R₄, which may be identical or different, are each chosen from alkyl groups comprising from 1 to 4 carbon atoms and hydroxyalkyl groups comprising from 1 to 4 carbon atoms;
n and p, which may be identical or different, are each chosen from integers ranging from 2 to 20; and
X⁻ is an anion chosen from anions derived from inorganic acids and anions derived from organic acids; and
(ii) polyquaternary ammonium polymers comprising repeating units of formula (V):

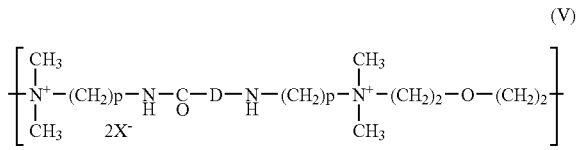

wherein:
p is an integer ranging from 1 to 6,
D is chosen from direct bonds and —(CH₂)ᵣ—CO— groups, wherein r is a number equal to 4 or 7, and
X– is an anion chosen from anions derived from inorganic acids and anions derived from organic acids, and
wherein:
a second compartment comprises at least one oxidizing agent and at least one cyclohomopolymer of dialkyl-diallylammonium comprising, as a constituent of the chain, at least one unit of structure (I):

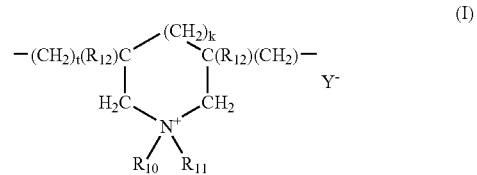

wherein:
k and t, which may be identical or different, are each chosen from 0 and 1, with the proviso that the sum of k+t is equal to 1;
R₁₂, which may be identical or different, are each chosen from hydrogen atoms and methyl groups;
R₁₀ and R₁₁, which may be identical or different, are each chosen from alkyl groups comprising from 1 to 22 carbon atoms, hydroxyalkyl groups, and C₁–C₄ amidoalkyl groups;
R₁₀ and R₁₁, together with the nitrogen atom to which they are commonly bonded, may additionally form at least one heterocyclic group;
Y⁻ is an anion.

90. A kit according to claim 89, wherein said keratin fibers are chosen from human keratin fibers.

91. A kit according to claim 90, wherein said human keratin fibers are human hair.

* * * * *

UNITED STATES PATENT AND TRADEMARK OFFICE
CERTIFICATE OF CORRECTION

PATENT NO. : 7,060,107 B2
APPLICATION NO. : 09/750717
DATED : June 13, 2006
INVENTOR(S) : Cécile Bebot et al.

It is certified that error appears in the above-identified patent and that said Letters Patent is hereby corrected as shown below:

On the Title Page, Item (75), in the Inventors, line 4, "Francoise" should read --Françoise--.

In claim 58, column 29, line 62, "$R^4$," should read --$R_4$,--.

Signed and Sealed this

Seventeenth Day of October, 2006

JON W. DUDAS
*Director of the United States Patent and Trademark Office*